United States Patent
Chen et al.

(10) Patent No.: US 10,117,635 B2
(45) Date of Patent: Nov. 6, 2018

(54) ELECTRONIC ACOUSTIC STETHOSCOPE WITH ECG

(71) Applicants: Guangren Chen, Acadia, CA (US); Rong Yang, Porter Ranch, CA (US)

(72) Inventors: Guangren Chen, Acadia, CA (US); Rong Yang, Porter Ranch, CA (US)

(*) Notice: Subject to any disclaimer, the term of this patent is extended or adjusted under 35 U.S.C. 154(b) by 0 days.

(21) Appl. No.: 15/712,469

(22) Filed: Sep. 22, 2017

(65) Prior Publication Data

US 2018/0028144 A1 Feb. 1, 2018

Related U.S. Application Data

(63) Continuation-in-part of application No. 15/393,135, filed on Dec. 28, 2016, now Pat. No. 9,999,364, (Continued)

(51) Int. Cl.
*A61B 5/04* (2006.01)
*A61B 7/04* (2006.01)
(Continued)

(52) U.S. Cl.
CPC .............. *A61B 7/04* (2013.01); *A61B 5/0006* (2013.01); *A61B 5/0245* (2013.01); *A61B 5/044* (2013.01);
(Continued)

(58) Field of Classification Search
CPC ..... A61B 7/04; A61B 5/04085; A61B 5/0006; A61B 5/04017; A61B 5/04014;
(Continued)

(56) References Cited

U.S. PATENT DOCUMENTS 6,757,392 B1* 6/2004 Granzotto ............ A61B 5/0002
181/131
8,320,576 B1* 11/2012 Abbruscato .............. A61B 7/04
381/67

(Continued)

OTHER PUBLICATIONS

Visual Electronic Stethoscope with Pulse Oximeter and ECG, CMS-VE, CMSVE, on http://www.facelake.com/stethoscope-cms-ve.html.

*Primary Examiner* — Mallika D Fairchild
(74) *Attorney, Agent, or Firm* — John R. Kasha; Kelly L. Kasha; Kasha Law LLC

(57) ABSTRACT

A noninvasive system for detecting and processing PCG and ECG waveforms includes an electronic acoustic stethoscope and a server computer. Heart sounds of a patient are measured using an acoustic transducer of a chestpiece of the electronic acoustic stethoscope, the heart sounds are sent to an earpiece of the electronic acoustic stethoscope, and a PCG waveform is created. Heart electrical signals of the patient are measured using at least four electrodes of the chestpiece and an ECG waveform is created. The PCG waveform and/or the ECG waveform are transmitted to the server computer using a wireless communication device of the chestpiece. The PCG waveform is processed for additional PCG information and/or the ECG waveform is processed for additional ECG information using the server computer. Access to the additional PCG information and/or additional ECG information is provided to at least one client device using the server computer.

16 Claims, 34 Drawing Sheets

Related U.S. Application Data which is a continuation-in-part of application No. 14/749,697, filed on Jun. 25, 2015, now Pat. No. 9,538,930, said application No. 14/749,697 is a continuation-in-part of application No. 14/662,996, filed on Mar. 19, 2015, now Pat. No. 9,339,204, which is a continuation of application No. PCT/US2015/020828, filed on Mar. 16, 2015.

(60) Provisional application No. 62/398,391, filed on Sep. 22, 2016, provisional application No. 62/271,704, filed on Dec. 28, 2015, provisional application No. 62/271,699, filed on Dec. 28, 2015, provisional application No. 62/017,185, filed on Jun. 25, 2014, provisional application No. 62/008,435, filed on Jun. 5, 2014.

(51) Int. Cl.
| | | |
|---|---|---|
| *A61B 5/0408* | (2006.01) | |
| *A61B 5/00* | (2006.01) | |
| *A61B 5/044* | (2006.01) | |
| *A61B 5/042* | (2006.01) | |
| *A61B 5/0245* | (2006.01) | |
| *A61B 5/0452* | (2006.01) | |
| *A61B 5/0464* | (2006.01) | |

(52) U.S. Cl.
CPC ...... *A61B 5/04014* (2013.01); *A61B 5/04017* (2013.01); *A61B 5/0422* (2013.01); *A61B 5/0452* (2013.01); *A61B 5/0464* (2013.01); *A61B 5/04085* (2013.01); *A61B 5/6823* (2013.01); *A61B 5/6869* (2013.01); *A61B 5/7278* (2013.01)

(58) Field of Classification Search
CPC ... A61B 5/0422; A61B 5/6823; A61B 5/6869; A61B 5/044
See application file for complete search history.

(56) References Cited

U.S. PATENT DOCUMENTS

| | | | | |
|---|---|---|---|---|
| 2002/0072682 | A1* | 6/2002 | Hopman | A61B 5/0006 600/509 |
| 2007/0073176 | A1* | 3/2007 | Healey | A61B 5/0468 600/517 |
| 2011/0105928 | A1* | 5/2011 | Bojovic | A61B 5/0006 600/515 |
| 2011/0245702 | A1* | 10/2011 | Clark | A61B 5/04284 600/523 |
| 2012/0296227 | A1* | 11/2012 | Chen | A61B 5/0402 600/509 |
| 2013/0009783 | A1* | 1/2013 | Tran | G06F 19/3418 340/669 |
| 2013/0116584 | A1* | 5/2013 | Kapoor | A61B 5/02 600/513 |
| 2015/0164340 | A1* | 6/2015 | Bedingham | A61B 7/04 600/484 |
| 2015/0327775 | A1* | 11/2015 | Carter | A61B 5/14551 600/301 |

* cited by examiner

ELECTRONIC ACOUSTIC STETHOSCOPE WITH ECG

CROSS REFERENCE TO RELATED APPLICATION

This application is a continuation in part of U.S. patent application Ser. No. 15/393,135, filed Dec. 28, 2016, which is a continuation in part of U.S. patent application Ser. No. 14/749,697, filed Jun. 25, 2015, now U.S. Pat. No. 9,538,930, which is a continuation in part of U.S. patent application Ser. No. 14/662,996, filed Mar. 19, 2015, now U.S. Pat. No. 9,339,204, which is a continuation of PCT Application No. PCT/US15/20828, filed Mar. 16, 2015, which claims the benefit of U.S. Provisional Patent Application Ser. No. 62/008,435, filed Jun. 5, 2014; this application also claims the benefit of U.S. Provisional Patent Application Ser. No. 62/398,391, filed Sep. 22, 2016; U.S. patent application Ser. No. 15/393,135 claims the benefit of U.S. Provisional Patent Application Ser. No. 62/271,704, filed Dec. 28, 2015, and U.S. Provisional Patent Application Ser. No. 62/271,699, filed Dec. 28, 2015; and U.S. patent application Ser. No. 14/749,697 claims the benefit of U.S. Provisional Patent Application Ser. No. 62/017,185, filed Jun. 25, 2014, the content of all of which is incorporated by reference herein in their entireties.

INTRODUCTION

The teachings herein relate to systems and methods for providing electrocardiography (ECG) measurements using an electronic acoustic stethoscope. More particularly, the teachings herein relate to a system including an electronic acoustic stethoscope, a server computer, and a client device. The electronic acoustic stethoscope acquires an ECG signal from a patient and wirelessly communicates the ECG signal to a server computer. The server computer processes the ECG signal. The client device accesses the server computer to obtain the processed ECG signal and provides the processed ECG signal and information about the processed ECG signal to a healthcare provider. The systems and methods herein can be performed in conjunction with a processor, controller, or computer system, such as the computer system of FIG. 1.

BACKGROUND

In the clinic, the stethoscope has been used for over 200 years and it is still an essential tool. Its main function is to test the phonocardiogram (PCG) and heart rate.

Stethoscope History

The stethoscope was invented in France in 1816 by René Laennec at the Necker-Enfants Malades Hospital in Paris. It consisted of a wooden tube and was monaural. Laennec invented the stethoscope because he was uncomfortable placing his ear on women's chests to hear heart sounds. His device was similar to the common ear trumpet, a historical form of hearing aid; indeed, his invention was almost indistinguishable in structure and function from the trumpet, which was commonly called a "microphone". Laennec called his device the "stethoscope" (stethoscope, "chest scope").

The first flexible stethoscope of any sort may have been a binaural instrument with articulated joints not very clearly described in 1829. In 1840, Golding Bird described a stethoscope he had been using with a flexible tube. Bird was the first to publish a description of such a stethoscope but he noted in his paper the prior existence of an earlier design (which he thought was of little utility), which he described as the snake ear trumpet. Bird's stethoscope had a single earpiece. In 1851, Irish physician Arthur Leared invented a binaural stethoscope, and in 1852 George Philip Cammann perfected the design of the stethoscope instrument (that used both ears) for commercial production, which has become the standard ever since. Cammann also wrote a major treatise on diagnosis by auscultation, which the refined binaural stethoscope made possible. By 1873, there were descriptions of a differential stethoscope that could connect to slightly different locations to create a slight stereo effect, though this did not become a standard tool in clinical practice. The medical historian Jacalyn Duffin has argued that the invention of the stethoscope marked a major step in the redefinition of disease from being a bundle of symptoms, to the current sense of a disease as a problem with an anatomical system even if there are no noticeable symptoms. This re-conceptualization occurred in part, Duffin argues, because prior to the stethoscopes, there were no non-lethal instruments for exploring internal anatomy. Rappaport and Sprague designed a new stethoscope in the 1940s, which became the standard by which other stethoscopes are measured, consisting of two sides, one of which is used for the respiratory system, the other for the cardiovascular system. The Rappaport-Sprague stethoscope was later made by Hewlett-Packard. HP's medical products division was spun off as part of Agilent Technologies, Inc., where it became Agilent Healthcare. Agilent Healthcare was purchased by Philips which became Philips Medical Systems, before the walnut-boxed, $300, original Rappaport-Sprague stethoscope was finally abandoned in 2004, along with Philips' brand (manufactured by Andromed, of Montreal, Canada) electronic stethoscope model. The Rappaport-Sprague model stethoscope was heavy and short (18-24 in [46-61 cm]) with an antiquated appearance recognizable by their two large independent latex rubber tubes connecting an exposed-leaf-spring-joined-pair of opposing "f"-shaped chrome-plated brass binaural ear tubes with a dual-head chestpiece.

Several other minor refinements were made to stethoscopes, until in the early 1960s David Littmann, a Harvard Medical School professor, created a new stethoscope that was lighter than previous models and had improved acoustics. In the late 1970s, 3M-Littmann introduced the tunable diaphragm: a very hard (G-10) glass-epoxy resin diaphragm member with an overmolded silicone flexible acoustic surround which permitted increased excursion of the diaphragm member in a "z"-axis with respect to the plane of the sound collecting area. The left shift to a lower resonant frequency increases the volume of some low frequency sounds due to the longer waves propagated by the increased excursion of the hard diaphragm member suspended in the concentric acoustic surround. Conversely, restricting excursion of the diaphragm by pressing the stethoscope diaphragm surface firmly against the anatomical area overlying the physiological sounds of interest, the acoustic surround could also be used to dampen excursion of the diaphragm in response to "z"-axis pressure against a concentric fret. This raises the frequency bias by shortening the wavelength to auscultate a higher range of physiological sounds.

In 1999, Richard Deslauriers patented the first external noise reducing stethoscope, the DRG Puretone. It featured two parallel lumens containing two steel coils which dissipated infiltrating noise as inaudible heat energy. The steel coil "insulation" added 0.30 lb to each stethoscope. In 2005, DRG's diagnostics division was acquired by TRIMLINE Medical Products. In 2015, Dr. Tarek Loubani announced an open-source 3D-printed stethoscope based on the 1960s-era Littmann Cardiology 3 stethoscope. The 3D-printed equivalent is nearly an order of magnitude more affordable than the aforementioned non-3D-printed stethoscope and is intended to make the medical device more accessible to obtain, particularly in developing countries.

Stethoscope Uses

Acoustic stethoscopes are familiar to most people, and operate on the transmission of sound from the chestpiece, via air-filled hollow tubes, to the listener's ears. The chestpiece usually consists of two sides that can be placed against the patient for sensing sound; a diaphragm (plastic disc) or bell (hollow cup). If the diaphragm is placed on the patient, body sounds vibrate the diaphragm, creating acoustic pressure waves which travel up the tubing to the listener's ears. If the bell is placed on the patient, the vibrations of the skin directly produce acoustic pressure waves traveling up to the listener's ears. The bell transmits low frequency sounds, while the diaphragm transmits higher frequency sounds. This two-sided stethoscope was invented by Rappaport and Sprague in the early part of the 20th century.

One problem with acoustic stethoscopes was that the sound level was extremely low. This problem was surmounted in 1999 with the invention of the stratified continuous (inner) lumen, and the kinetic acoustic mechanism in 2002. Acoustic stethoscopes are the most commonly used. A recent independent review evaluated twelve common acoustic stethoscopes on the basis of loudness, clarity, and ergonomics. They did acoustic laboratory testing and recorded heart sounds on volunteers. The results were listed by brand and model.

An electronic stethoscope (or stethophone) overcomes the low sound levels by electronically amplifying body sounds. However, amplification of stethoscope contact artifacts and component cutoffs (frequency response thresholds of electronic stethoscope microphones, pre-amps, amps, and speakers) limit electronically amplified stethoscopes' overall utility by amplifying mid-range sounds, while simultaneously attenuating high- and low-frequency range sounds. Currently, a number of companies offer electronic stethoscopes.

Electronic stethoscopes require conversion of acoustic sound waves to electrical signals which can then be amplified and processed for optimal listening. Unlike acoustic stethoscopes, which are all based on the same physics, transducers in electronic stethoscopes vary widely. The simplest and least effective method of sound detection is achieved by placing a microphone in the chestpiece. This method suffers from ambient noise interference and has fallen out of favor. Another method, used in Welch-Allyn's Meditron stethoscope, comprises placement of a piezoelectric crystal at the head of a metal shaft, the bottom of the shaft making contact with a diaphragm. 3M also uses a piezo-electric crystal placed within foam behind a thick rubber-like diaphragm. The Thinklabs' Rhythm 32 uses an electromagnetic diaphragm with a conductive inner surface to form a capacitive sensor. This diaphragm responds to sound waves, with changes in an electric field replacing changes in air pressure. The EkoCore enables wireless transmission of heart sounds to a smartphone or tablet. Because the sounds are transmitted electronically, an electronic stethoscope can be a wireless device, can be a recording device, and can provide noise reduction, signal enhancement, and both visual and audio output.

Around 2001, Stethographics introduced PC-based software which enabled a phonocardiograph, graphic representation of cardiologic and pulmonologic sounds to be generated, and interpreted according to related algorithms. All of these features are helpful for purposes of telemedicine (remote diagnosis) and teaching. Electronic stethoscopes are also used with Computer-aided Auscultation programs to analyze the recorded heart sounds pathological or innocent heart murmurs.

Some electronic stethoscopes feature direct audio output that can be used with an external recording device, such as a laptop or MP3 recorder. The same connection can be used to listen to the previously recorded auscultation through the stethoscope headphones, allowing for more detailed study for general research as well as evaluation and consultation regarding a particular patient's condition and telemedicine, or remote diagnosis.

There are some smartphone apps that can use the phone as a stethoscope. At least one uses the phone's own microphone to amplify sound, produce a visualization, and e-mail the results. These apps may be used for training purposes or as novelties, but have not yet gained acceptance for professional medical use. The first stethoscope that could work with a smartphone application was introduced in 2015 and used to listen to a patient's small intestine.

Stethoscopes are often considered as a symbol of healthcare professionals, as various healthcare providers are often seen or depicted with stethoscopes hanging around their necks. A 2012 research paper claimed that the stethoscope, when compared to other medical equipment, had the highest positive impact on the perceived trustworthiness of the practitioner seen with it.

The advent of practical, widespread portable ultrasonography (point-of-care ultrasonography) in the late 1990s to early 2000s led some physicians to ask how soon it would be before stethoscopes would become obsolete. Others answered that they thought the relationship between the various tools (stethoscopes and digital devices) would change but that it would be a long time before stethoscopes were obsolete. A decade later, in 2016, the same two sides of the argument are still being made.

One cardiologist said, "the stethoscope is dead", but a pediatrician said, "we are not at the place, and probably won't be for a very long time", where stethoscopes were obsolete. One consideration is that it depends on the segment of health care (emergency medical services, nursing, and medicine) and the specialty. "Stethoscopes retain their value for listening to lungs and bowels for clues of disease, experts agree." But for the cardiovascular system, "auscultation is superfluous", one cardiologist said. Thus, it could be that cardiology in the secondary and tertiary care settings may abandon the stethoscope many years before primary care, pediatrics, and physical therapy do.

ECG History

Electrical signals produced by a human heart were observed through electrodes attached to a patient's skin as early as 1879. Between 1897 and 1911 various methods were used to detect these electrical signals and record a heartbeat in real-time. In 1924, Willem Einthoven was awarded the Nobel Prize in medicine for identifying the various waveforms of a heartbeat and assigning the letters P, Q, R, S, T, U, and J to these waveforms. Since the early 1900s, the equipment used for electrocardiography (ECG or EKG) has changed. However, the basic waveforms detected and analyzed have not changed.

An ECG device detects electrical impulses or changes in the electrical potential between two electrodes attached to the skin of a patient as the heart muscle contracts or beats. Electrically, the contraction of the heart is caused by depolarization and repolarization of various parts of the heart muscle. Initially, or at rest, the muscle cells of the heart have a negative charge. In order to cause them to contract, they receive an influx of positive ions Na$^+$ and Ca$^{++}$. This influx of positive ions is called depolarization. The return of negative ions to bring the heart back to a resting state is called repolarization. Depolarization and repolarization of the heart affect different parts of the heart over time giving rise to the P, Q, R, S, T, U, and J waveforms.

FIG. 2 is an exemplary plot 200 of the P, Q, R, S, and T waveforms of a conventional ECG waveform of a heartbeat from a conventional ECG device. The P, Q, R, S, and T waveforms represent electrical conduction through a heart muscle. P waveform 210 represents the propagation of depolarization from the sinoatrial node, to the right and left atriums, and to the atrioventricular node. The sinoatrial node is also referred to as the sinus node, SA node, or SAN. The atrioventricular node is also referred to as the AV node or AVN. The right atrium is also referred to as the RA, and the left atrium is also referred to as the LA.

FIG. 3 is an exemplary diagram 300 of the depolarization of the muscle tissue of a heart that produces P waveform 210 of FIG. 2 as detected by a conventional ECG device. P waveform 210 of FIG. 2 is produced as depolarization propagates from SAN 310 to AVN 340 in FIG. 3. As depolarization propagates from SAN 310 to AVN 340, it also spreads from RA 320 to LA 340. P waveform 210 of FIG. 2 typically has a duration of 80 ms, for example.

PR segment 220 of FIG. 2 represents the propagation of depolarization from the AVN to the Bundle of His, and then to the Bundle Branches. PR segment 230 may also include depolarization to the Purkinje fibers of the inner ventricular walls. The Bundle of His is also referred to as the His Bundle or His. The Bundle Branches include the right bundle branches (RBB) and the left bundle branches (LBB). As shown in FIG. 2, in a conventional ECG, PR segment 220 shows up as a flat line or waveform with no amplitude.

FIG. 4 is an exemplary diagram 400 of the depolarization of the muscle tissue of a heart that produces PR segment 220 of FIG. 2 as detected by a conventional ECG device. PR segment 220 of FIG. 2 is produced as depolarization propagates from AVN 340 to His 450 and then to Bundle Branches 460 that include RBB 461 and LBB 462. PR segment 220 of FIG. 2 typically has a duration of between 50 and 120 ms, for example.

Waveforms Q 230, R 240, and S 250 of FIG. 2 form the QRS complex. The QRS complex represents the propagation of depolarization through the right and left ventricles. The right ventricle is also referred to as RV, and the left ventricle is referred to as LV.

FIG. 5 is an exemplary diagram 500 of the depolarization of the muscle tissue of a heart that produces Q waveform 230, R waveform 240, and S waveform 250 of FIG. 2 as detected by a conventional ECG device. Waveforms Q 230, R 240, and S 250 of FIG. 2 produced as depolarization propagates from Bundle Branches 460 through RV 571 and LV 572. RV 571 and LV 572 have the largest muscle mass in the heart. The QRS complex formed by waveforms Q 230, R 240, and S 250 of FIG. 2 typically has a duration of between 80 and 100 ms, for example.

ST segment 260 of FIG. 2 represents the period during which the ventricles remain depolarized and contracted. As shown in FIG. 2, in a conventional ECG, ST segment 260 shows up as a flat line or waveform with no amplitude. ST segment 260 typically has a duration of between 80 and 120 ms, for example.

The point in FIG. 2 at which the QRS complex ends and ST segment 260 begins is called J point 255. A J waveform (not shown) can sometimes appear as an elevated J point at J point 255 or as a secondary R waveform. A J waveform is usually characteristic of a specific disease. The J waveform is also referred to as the Osborn wave, camel-hump sign, late delta wave, hathook junction, hypothermic wave, prominent J wave, K wave, H wave or current of injury.

T waveform 270 of FIG. 2 represents the repolarization or recovery of the ventricles. T waveform 270 typically has a duration of 160 ms, for example. The interval between the Q and T waveforms is referred to as the QT interval.

FIG. 6 is an exemplary diagram 600 of the repolarization of the muscle tissue of a heart that produces T waveform 270 of FIG. 2 as detected by a conventional ECG device. As shown in FIG. 6, RV 571 and LV 572 are repolarized.

Not shown in FIG. 2 is the U waveform. The U waveform sometimes appears after the T waveform. The U waveform is thought to represent repolarization of the interventricular septum, the papillary muscles, or the Purkinje fibers.

As shown in FIGS. 3 through 6, as a heart beats, electrical signals flow through all the different muscle tissues of the heart. As shown in FIG. 2, for the last 100 years conventional ECG devices have been able to detect some of these signals in the form of the P, Q, R, S, T, U, and J waveforms. These waveforms have aided in the diagnosis and treatment of many heart problems. Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

Stethoscope ECG

Recently, many additional measurement functions have been added to stethoscopes including ECG. For example, a visual electronic stethoscope with pulse oximeter and ECG has been developed. In addition, to measuring heart sounds, the visual electronic stethoscope with pulse oximeter and ECG can measure a conventional ECG waveform, like the waveform of FIG. 2. The conventional ECG waveform is displayed on a display of the visual electronic stethoscope with pulse oximeter and ECG.

The measurement side of the visual electronic stethoscope with pulse oximeter and ECG includes three electrodes for measuring a conventional ECG waveform. The measurement side of the visual electronic stethoscope with pulse oximeter and ECG also includes a piezoelectric sensor for measuring heart sounds. The visual electronic stethoscope with pulse oximeter and ECG also includes a separate finger probe for measuring pulse oxygen levels.

Although ECG measurement has been combined with a stethoscope in existing systems, such systems are not currently capable of advanced signal processing of ECG signals. As a result, the ECG measurement provided by such systems is limited. In addition, the displays of such systems are generally small, thus limiting the amount of information that can be displayed at any one time.

As a result, improved systems and methods are needed to combine stethoscopes with ECG measurement to provide advanced signal processing of ECG signals and to provide detailed information to healthcare providers.

Before one or more embodiments of the invention are described in detail, one skilled in the art will appreciate that the invention is not limited in its application to the details of construction, the arrangements of components, and the arrangement of steps set forth in the following detailed description. The invention is capable of other embodiments and of being practiced or being carried out in various ways. Also, it is to be understood that the phraseology and terminology used herein is for the purpose of description and should not be regarded as limiting.

DETAILED DESCRIPTION

Computer-Implemented System

Figure 1:
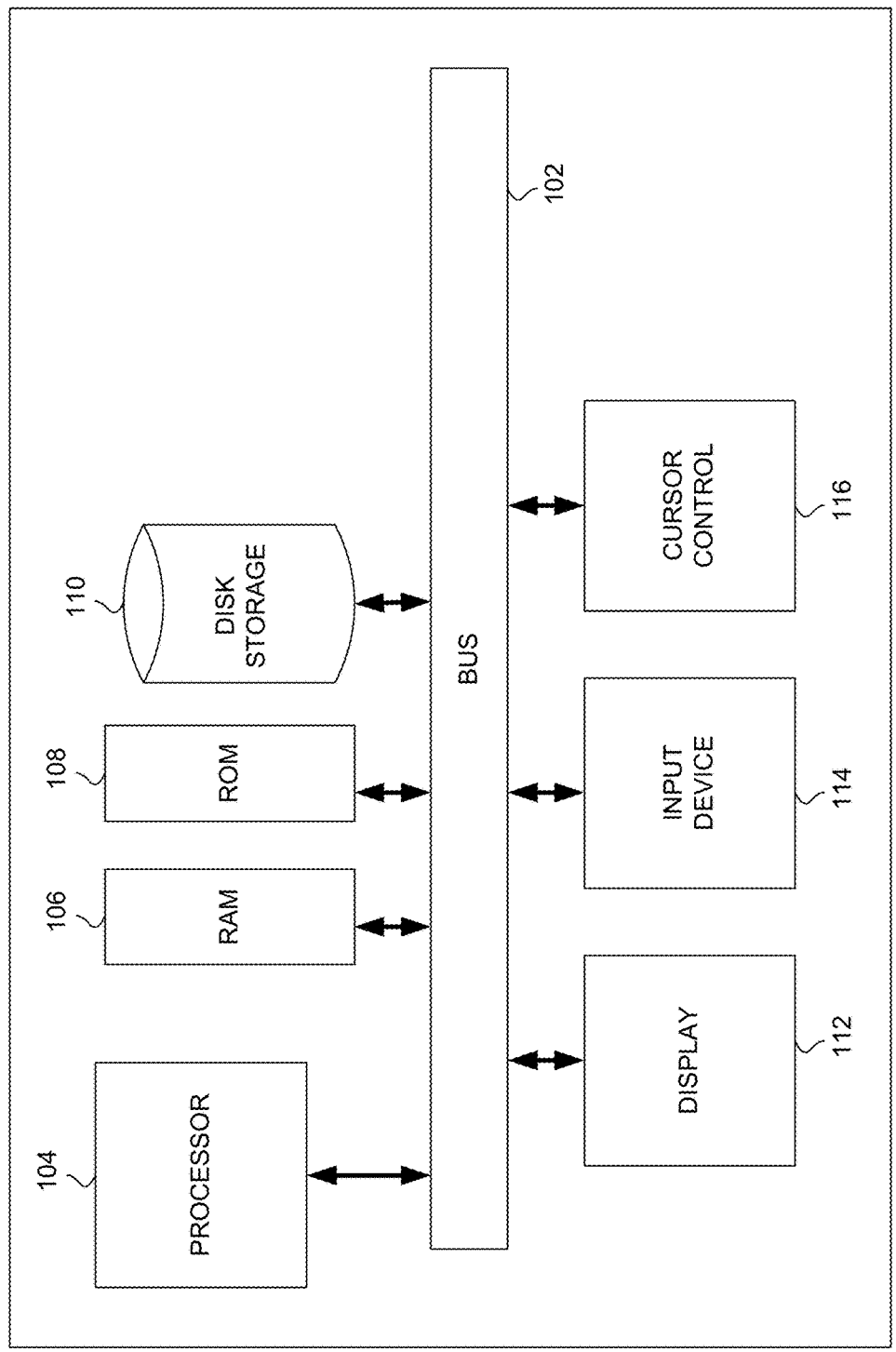
FIG. 1 is a block diagram that illustrates a computer system, in accordance with various embodiments.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Subwaveform Detection of the P, Q, R, S, T, U, and J Waveforms

As described above, electrical signals flow through all the different muscle tissues of the heart. For the last 100 years, conventional ECG devices have been able to detect some of these signals in the form of the P, Q, R, S, T, U, and J waveforms. These waveforms have aided in the diagnosis and treatment of many heart problems.

Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

In various embodiments, additional information is obtained from the electrical signals produced by a heart through signal processing. More specifically, signal processing is added to an ECG device in order to detect more information from the electrical signals that flow through all the different muscle tissues of the heart as it is beating.

Figure 7:
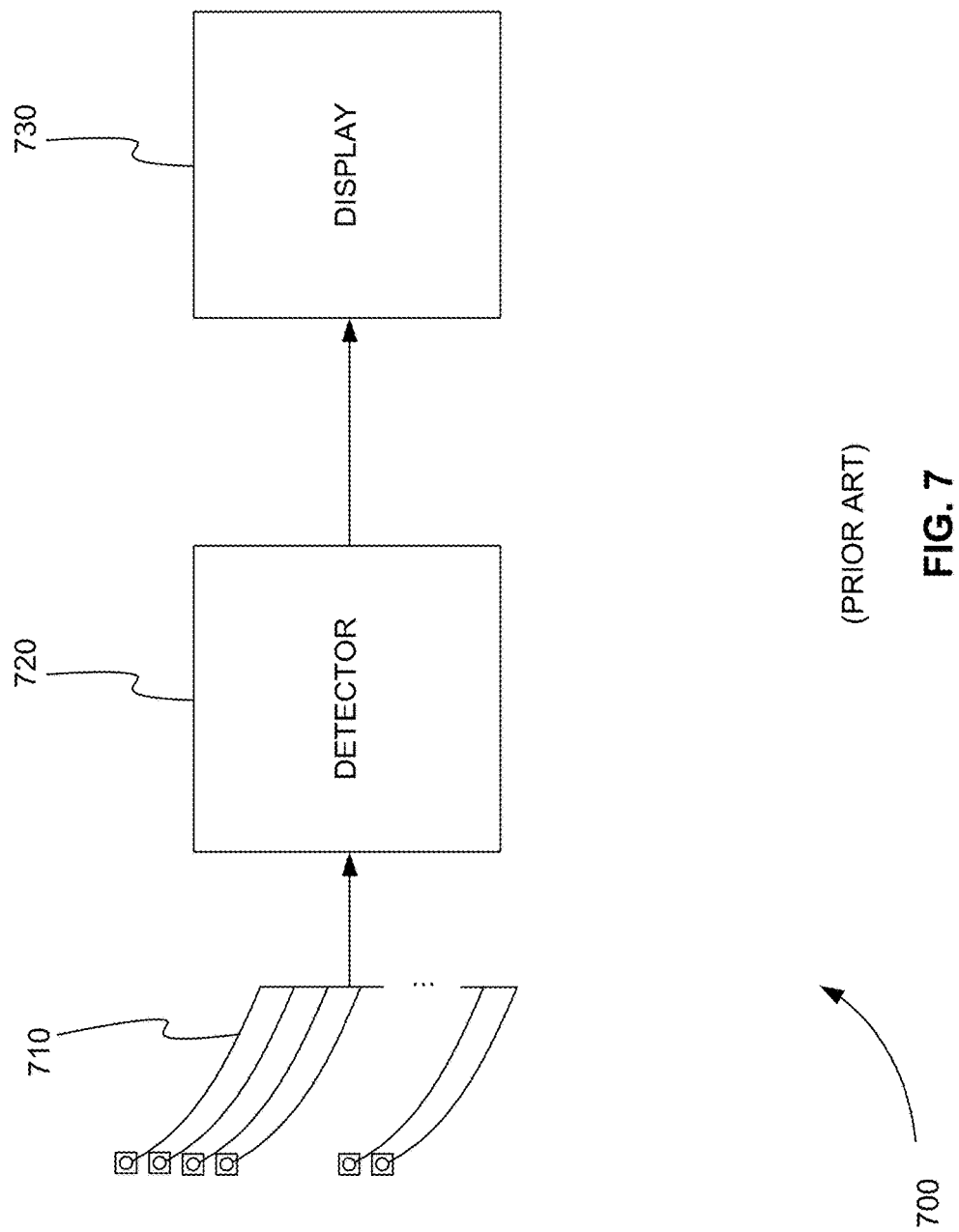
FIG. 7 is a block diagram of a conventional ECG device.

FIG. 7 is a block diagram 700 of a conventional ECG device. The conventional ECG device includes two or more leads or electrodes 710. Electrodes 710 are typically attached to the skin of a patient. Electrical signals produced by a beating heart are detected between pairs of electrodes 710. Because the heart is three-dimensional, electrodes are attached at different locations on a body to detect signals at different corresponding locations or angles from the heart. In other words, the electrodes are placed on a body to partially surround the heart. One typical type of ECG includes 12 electrodes, for example.

A voltage signal is detected between two electrodes 710 by detector 720. Detector 720 also typically amplifies the voltage signal. Detector 720 can also convert the voltage signal to a digital voltage signal using an analog to digital converter (A/D).

Detector 720 provides the detected and amplified voltage signal from each pair of electrodes 710 to display 730. Display 730 can be an electronic display device including, but not limited to, a cathode ray tube (CRT) device, light emitting diode (LED) device, or Liquid crystal display (LCD) device. Display 730 can also be a printer device. Additionally, display 730 can include a memory device to record detected signals. The memory device can be, but is not limited to, a volatile electronic memory, such as random access memory (RAM), a non-volatile electronic memory, such as electrically erasable programmable read-only memory (EEPROM or Flash memory), or a magnetic hard drive.

Figure 2:
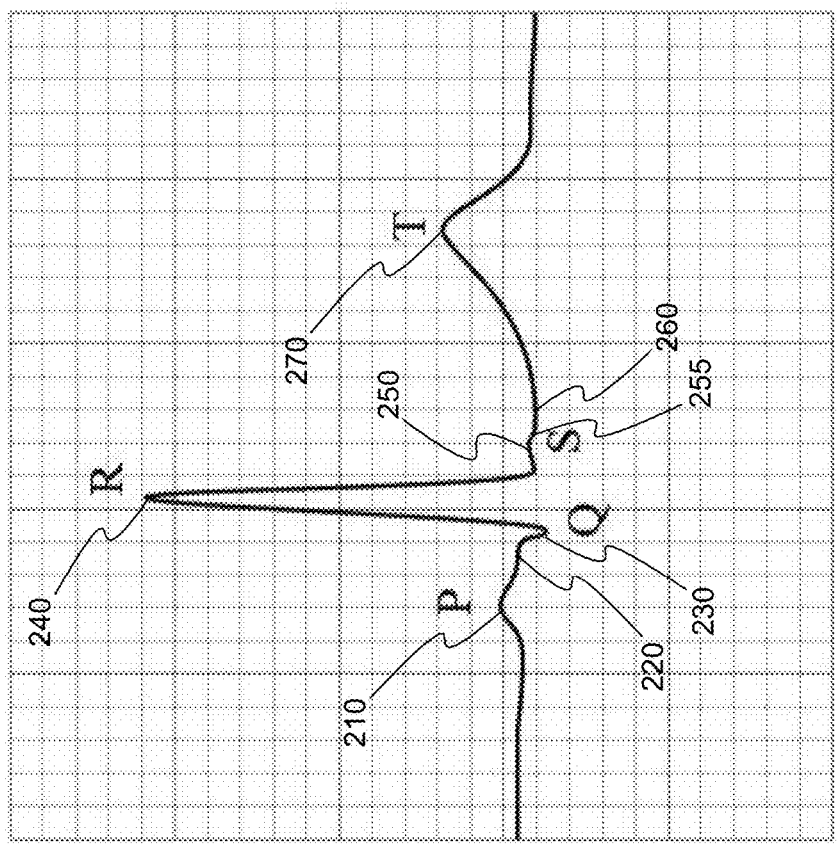
FIG. 2 is an exemplary plot of the P, Q, R, S, and T waveforms of a conventional electrocardiography (ECG) waveform of a heartbeat from a conventional ECG device.
Figure 3:
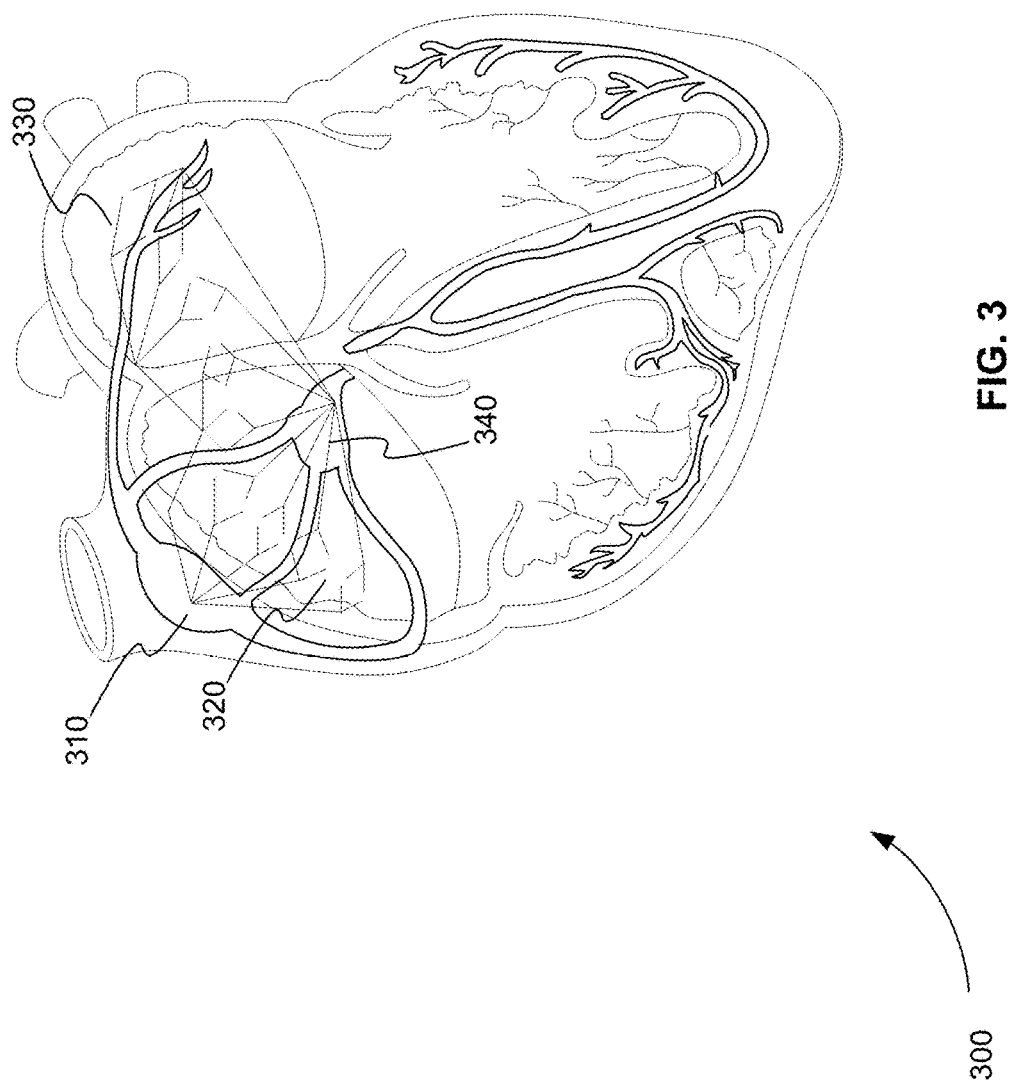
FIG. 3 is an exemplary diagram of the depolarization of the muscle tissue of a heart that produces the P waveform of FIG. 2 as detected by a conventional ECG device.
Figure 4:
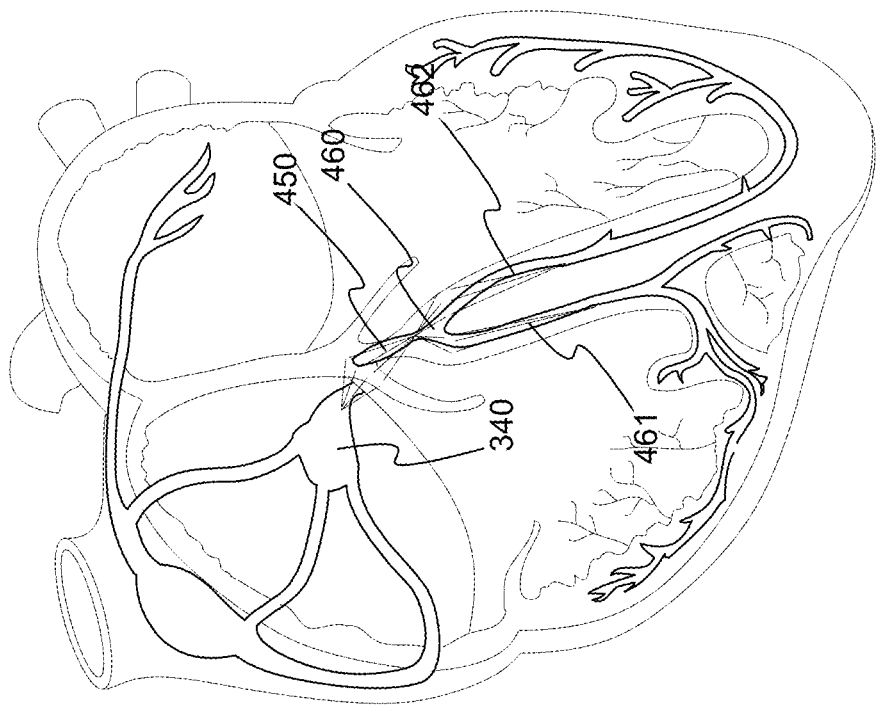
FIG. 4 is an exemplary diagram of the depolarization of the muscle tissue of a heart that produces the PR segment of FIG. 2 as detected by a conventional ECG device.
Figure 5:
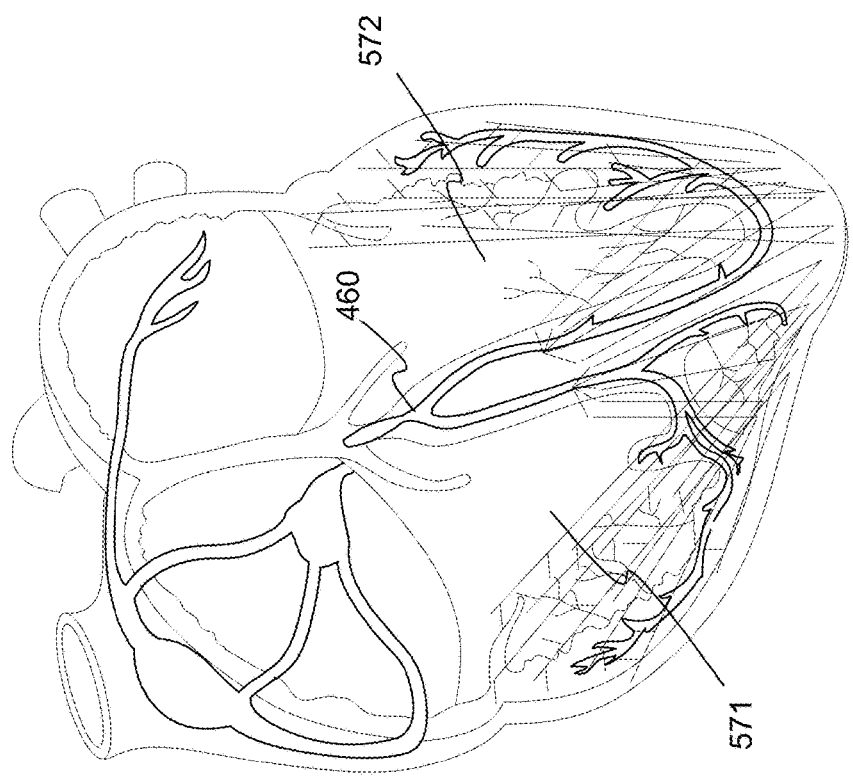
FIG. 5 is an exemplary diagram of the depolarization of the muscle tissue of a heart that produces the Q waveform, the R waveform, and the S waveform of FIG. 2 as detected by a conventional ECG device.
Figure 6:
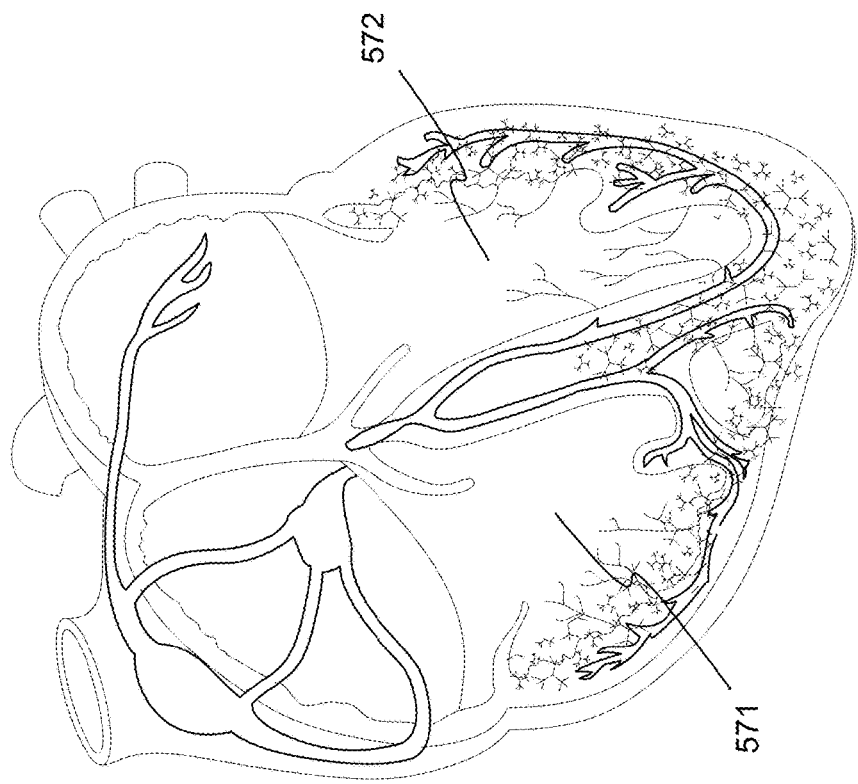
FIG. 6 is an exemplary diagram of the repolarization of the muscle tissue of a heart that produces the T waveform of FIG. 2 as detected by a conventional ECG device.

Display 730 displays a continuous loop of the detected P, Q, R, S, T, U, and J waveforms as shown in FIG. 2 for each pair of electrodes 710. Modern ECG devices can also include a processor (not shown), such as the processor shown in FIG. 1, to analyze the P, Q, R, S, T, U, and J waveforms. For example, the processor can calculate the time periods of the P, Q, R, S, T, U, and J waveforms and the times between the P, Q, R, S, T, U, and J waveforms. The processor can also compare this timing information to stored normal information. Based on the comparison, the processor can determine differences from the normal data. All information calculated by the processor can also be displayed on display 730.

Figure 8:
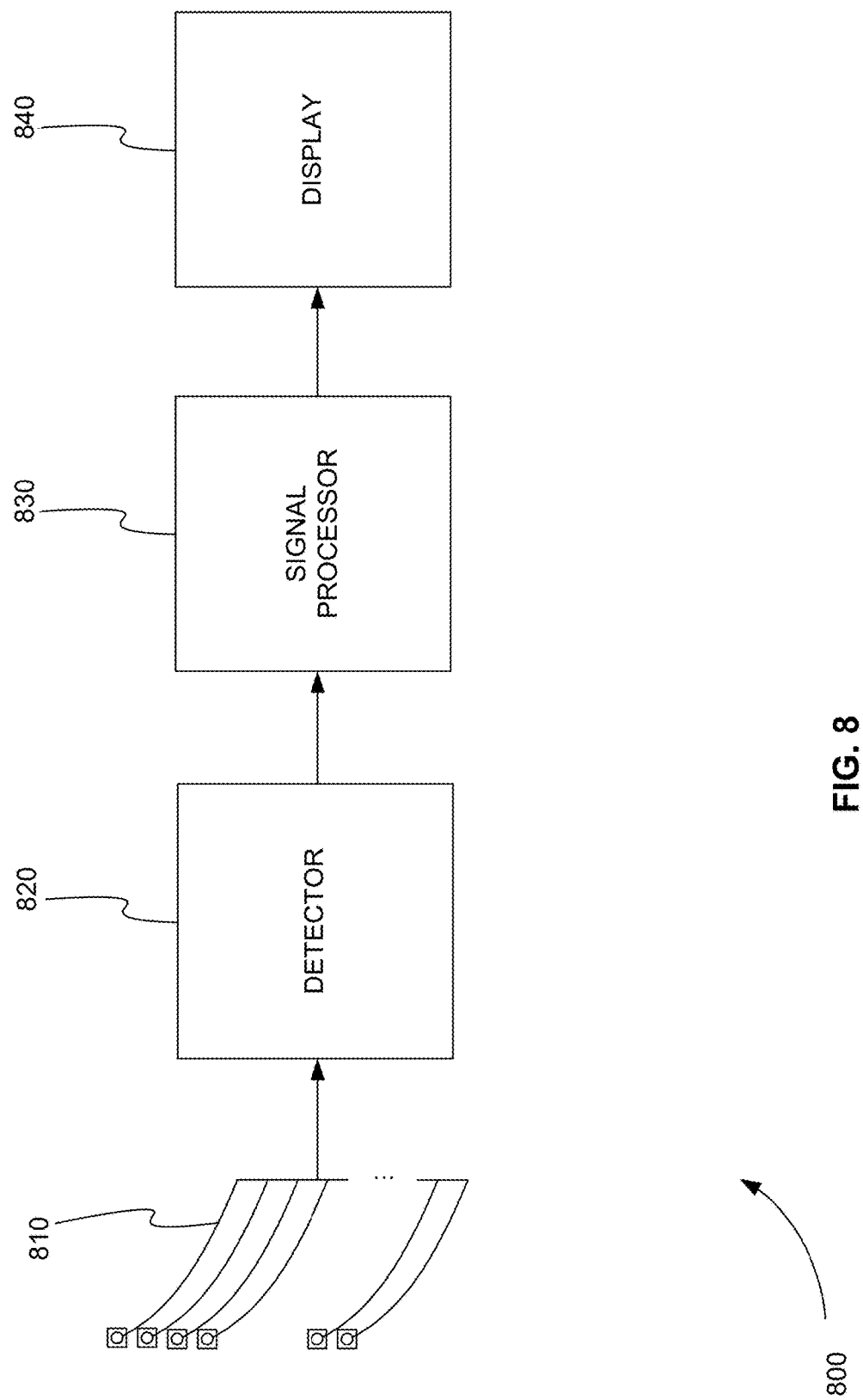
FIG. 8 is a block diagram of an ECG device for detecting more information from the electrical signals that flow through all the different muscle tissues of the heart as it is beating, in accordance with various embodiments.

FIG. 8 is a block diagram 800 of an ECG device for detecting more information from the electrical signals that flow through all the different muscle tissues of the heart as it is beating, in accordance with various embodiments. Electrodes 810 are attached to the skin of a patient, for example. Electrical signals produced by a beating heart are detected between pairs of electrodes 810.

A voltage signal is detected between two electrodes 810 by detector 820. Detector 820 also amplifies the voltage signal. Detector 820 also converts the voltage signal to a digital voltage signal using an analog to digital converter (A/D).

Detector 820 provides the detected and amplified voltage signal from each pair of electrodes 810 to signal processor 830. Detector 820 can also provide the detected and amplified voltage signal from each pair of electrodes 810 directly to display device 840 to display the conventional P, Q, R, S, T, U, and J waveforms.

Signal processor 830 detects or calculates one or more subwaveforms within and/or in the interval between the P, Q, R, S, T, U, and J waveforms of each detected and amplified voltage signal. A waveform is a shape or form of a signal. A subwaveform is shape or form of a signal that is within or part of another signal.

Signal processor 830 can be a separate electronic device that can include, but is not limited to, an application specific integrated circuit (ASIC), a field programmable gate array (FPGA), or a general purpose processor. Signal processor 830 can be software implemented on another processor of the ECG device, such as a processor of display device 840. Signal processor 830 can also be a remote server that receives the detected and amplified voltage signal from detector 820, detects or calculates one or more subwaveforms within and/or in the interval between the P, Q, R, S, T, U, and J waveforms, and sends the detected and amplified voltage signal and the one or more subwaveforms to display device 840.

Signal processor 830 sends one or more subwaveforms of each detected and amplified voltage signal to display device 840. Signal processor 830 can also calculate and send to the display device 840 the time periods of the one or more subwaveforms, the times between the one or more subwaveforms, and the times of the one or more subwaveforms in relation to the P, Q, R, S, T, U, and J waveforms and or the intervals between the P, Q, R, S, T, U, and J waveforms. Signal processor 830 can also compare this timing information to stored normal timing information. Based on the comparison, signal processor 830 can determine differences from the normal data and send this difference information and any of the timing information to display device 840.

Display device 840 displays a continuous loop of the one or more subwaveforms for each pair of electrodes 810. Display device 840 can also display part or all of the conventional P, Q, R, S, T, U, and J waveforms for comparison with the one or more subwaveforms. Like display 730 of FIG. 7, display device 840 of FIG. 8 can be an electronic display device, a printer, or any combination of the two.

In various embodiments, an ECG device using signal processing to detect one or more subwaveforms within the P, Q, R, S, T, U, and J waveforms and/or within the intervals between the P, Q, R, S, T, U, and J waveforms is herein referred to as a saah ECG device. The voltage difference signals produced by a saah ECG device are referred to as saah ECG waveforms. The term "saah" is an acronym for some of the anatomically distinct portions of muscle tissue that produce subwaveforms. Specifically, saah stands for sinoatrial node (SAN), atria (right atrium (RA) and left atrium (LA)), atrioventricular node (AVN), and bundle of His (HIS). However, a saah ECG waveform is not limited to including subwaveforms representing the SAN, the atria, the AVN, and the HIS. A saah ECG waveform can include any subwaveform the P, Q, R, S, T, U, and J waveforms and/or within the intervals between the P, Q, R, S, T, U, and J waveforms.

Figure 9:
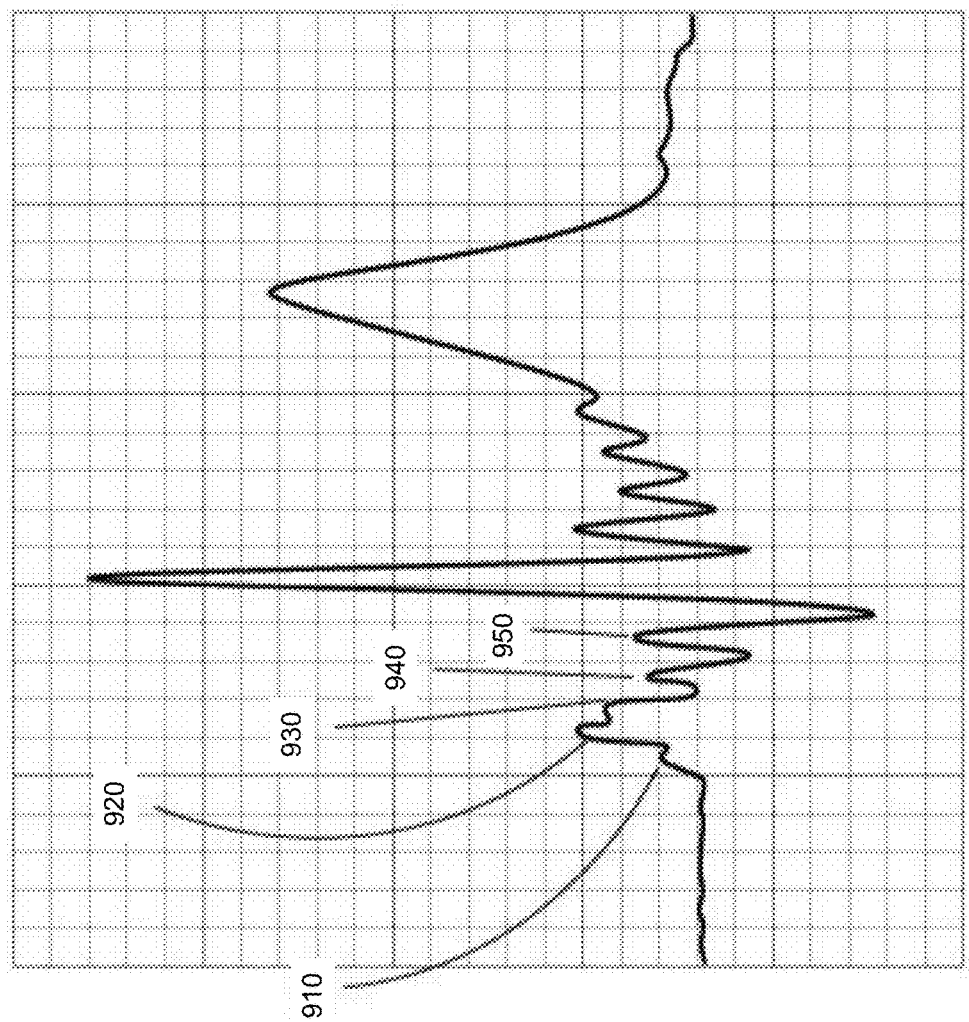
FIG. 9 is an exemplary plot of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments.

FIG. 9 is an exemplary plot 900 of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments. For example, five subwaveforms 910-950 of FIG. 9 are detected within the P waveform and the PR segment. The time period that includes the P waveform and the PR segment is also called the PR interval. Subwaveform 910 represents the depolarization of the SAN. Subwaveform 920 represents the depolarization of RA and LA. Subwaveform 930 represents the depolarization of the AVN. Subwaveform 940 represents the depolarization HIS. Finally, subwaveform 950 represents the depolarization of the bundle branches (BB).

In various embodiments, the subwaveforms of a saah ECG waveform are detected using signal processing. Electrodes 810 of the saah ECG of FIG. 8, for example, receive electrical impulses from anatomically distinct portions of muscle tissue or cells. The electrical impulses of anatomically distinct portions of muscle tissue of the heart have distinct frequencies. Through animal and human experimentation, the distinct frequency, frequency range, or frequency band of the anatomically distinct portions of muscle tissue of the heart are found. These distinct frequency bands of anatomically distinct portions of muscle tissue of the heart provide predetermined data or information for signal processing. In other words, the band pass frequency filtering of the signal processing is determined from the experimental data collected. A saah ECG device then employs one or more frequency band pass filters to detect the one or more subwaveforms.

Figure 10:
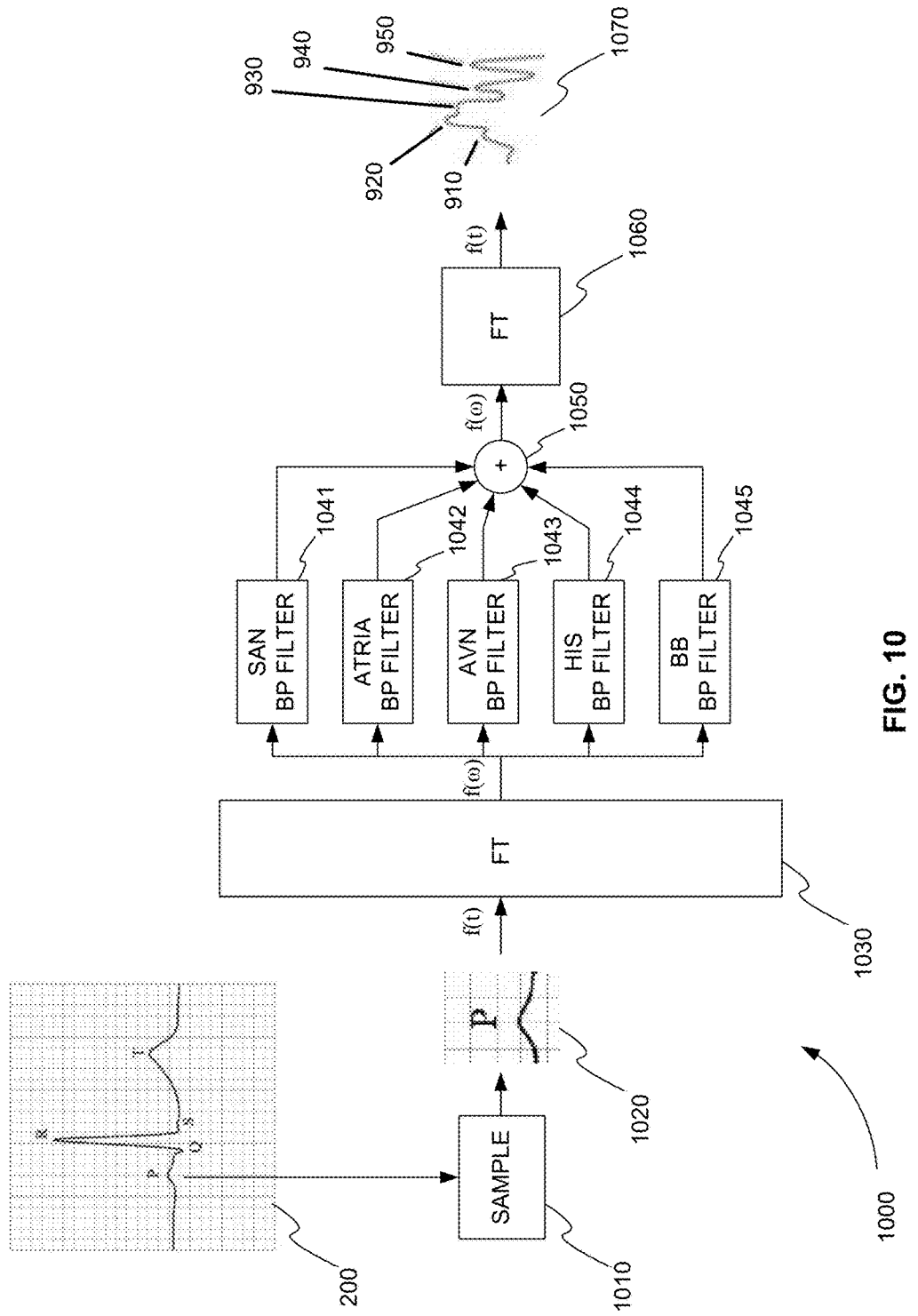
FIG. 10 is an exemplary block diagram showing a signal processing algorithm for detecting five subwaveforms within the PR interval of a conventional ECG waveform, in accordance with various embodiments.

FIG. 10 is an exemplary block diagram 1000 showing a signal processing algorithm for detecting five subwaveforms within the PR interval of a conventional ECG waveform, in accordance with various embodiments. Sampling block 1010 samples the electrical impulses in the PR interval time period of each heart. This is shown graphically in FIG. 1000 by separating PR interval 1020 from ECG waveform 200. The electrical impulses in the PR interval time period are sampled using electrodes 810 and detector 820 of FIG. 8, for example. Detector 820 of FIG. 8 can also amplify and convert the analog signal into a digital signal for digital processing.

The signal processing can be performed directly on the time domain signal received from a detector or the time domain signal received from a detector can be converted to the frequency domain for algorithmic processing. In FIG. 10, block 1030 converts the PR interval time domain signal to a PR interval frequency domain signal. The time domain signal is converted into a frequency domain signal using a Fourier transform, for example.

As described above, through animal and/or human experimentation, the frequency bands associated with depolarization of the SAN, atria, AVN, HIS, and BB of the heart are determined. Based on these frequency bands, band pass filters are created. Blocks 1041-1045 represent the band pass filters created to filter the PR interval frequency domain signal for frequency bands of the SAN, atria, AVN, HIS, and BB of the heart, respectively.

In block 1050, the frequency domain subwaveforms detected from the band pass filtering the frequency bands of the SAN, atria, AVN, HIS, and BB of the heart are summed. In block 1060, the filtered and summed frequency domain signal of the PR interval is converted back to a time domain signal. The frequency domain signal is converted into a time domain signal using a Fourier transform, for example.

The PR interval filtered and summed time domain signal 1070 includes five time domain subwaveforms 910-950. Subwaveforms 910-950 represent depolarization of the SAN, atria, AVN, HIS, and BB of the heart, respectively. Time domain signal 1070 can be used to replace PR interval 1020 in ECG waveform 200, for example. As a result, a saah ECG waveform is produced.

FIG. 10 shows a signal processing algorithm for detecting five subwaveforms. However, similar steps can be applied to detect fewer than five waveforms or more than five waveforms. Also, the steps of FIG. 10 describe detecting subwaveforms within the PR interval. However, similar steps can be applied to detect subwaveforms within the P, Q, R, S, T, U, and J waveforms and/or within one or more of the intervals between the P, Q, R, S, T, U, and J waveforms. In addition, the steps of FIG. 10 describe converting time signals to the frequency domain and then back to the time domain. One of ordinary skill in the art can appreciate that band pass filters can be applied directly to the time domain signal to provide the same result.

Figure 11:
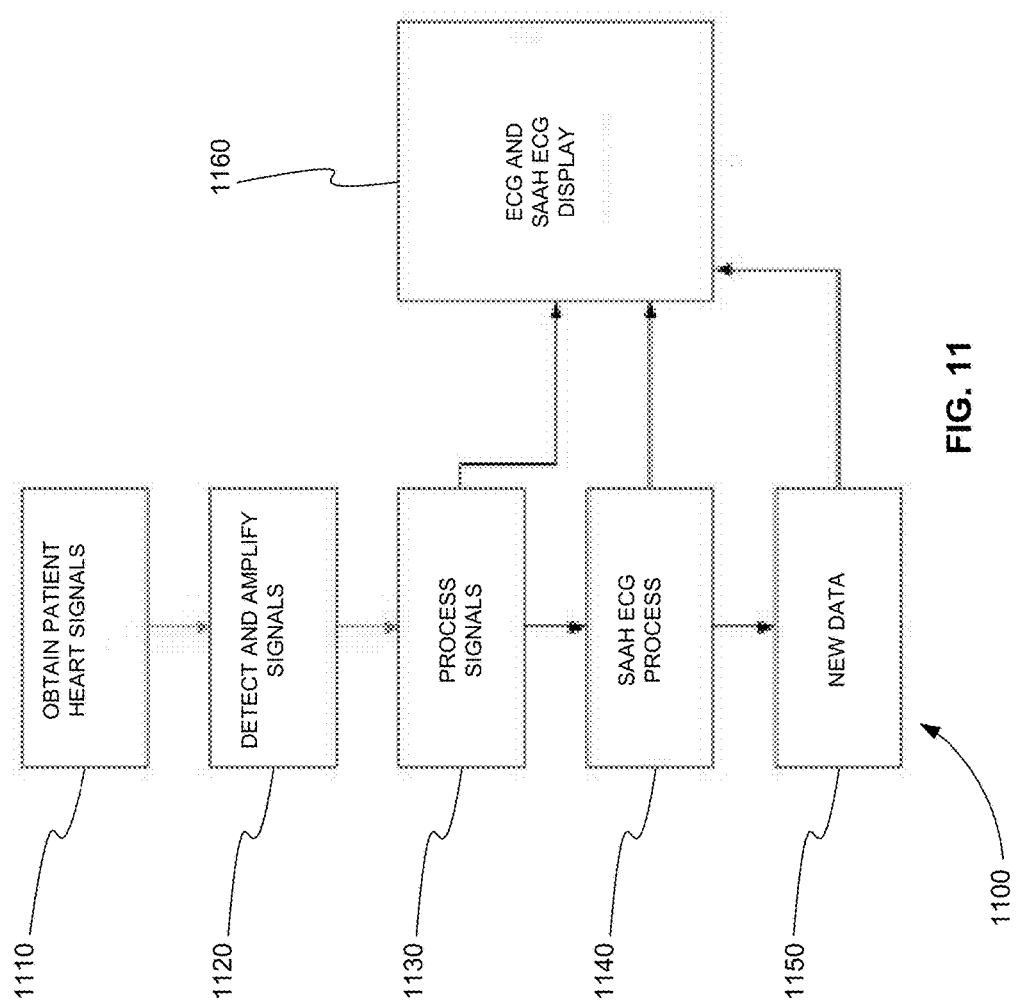
FIG. 11 is an exemplary block diagram of a saah ECG device that displays conventional ECG waveforms, saah ECG waveforms, and saah ECG data, in accordance with various embodiments.

FIG. 11 is an exemplary block diagram 1100 of a saah ECG device that displays conventional ECG waveforms, saah ECG waveforms, and saah ECG data, in accordance with various embodiments. In block 1110, patient heart signals are obtained. These heart signals can be obtained through noninvasive electrodes placed on the skin, such as electrodes 810 shown in FIG. 8. In various embodiments, heart signals may also be obtained using invasive electrodes placed directly on the heart. In block 1120, the heart signals are detected using a detector and amplified.

In block 1130, the detected and amplified heart signals are processed using a signal processor. The signal processor detects the conventional P, Q, R, S, T, U, and J waveforms and sends them to the display of block 1160. The signal processor also detects or calculates subwaveforms within the conventional P, Q, R, S, T, U, and J waveforms and/or within intervals between the conventional P, Q, R, S, T, U, and J waveforms. The signal processor sends the subwaveforms to block 1140 for further processing. The processor of block 1140 produces the saah ECG waveform that includes the subwaveforms and sends the saah ECG waveform to the display of block 1160. The processor of block 1140 calculates additional information or new data from the saah ECG waveform. This new data can include, but is not limited to, timing information about the subwaveforms, timing information about the intervals between the subwaveforms, and timing information about the subwaveforms and their relation to the conventional P, Q, R, S, T, U, and J waveforms. In block 1150, this new data is sent to the display of block 1160.

The display of block 1160 displays a continuous loop of the conventional ECG waveform, the saah ECG waveform, and the new data from the subwaveforms. The display of block 1160 can display this information on an electronic display or print it on paper. The display of block 1160 can also record this information. The display of block 1160 can record this information on any type of memory device.

Figure 12:
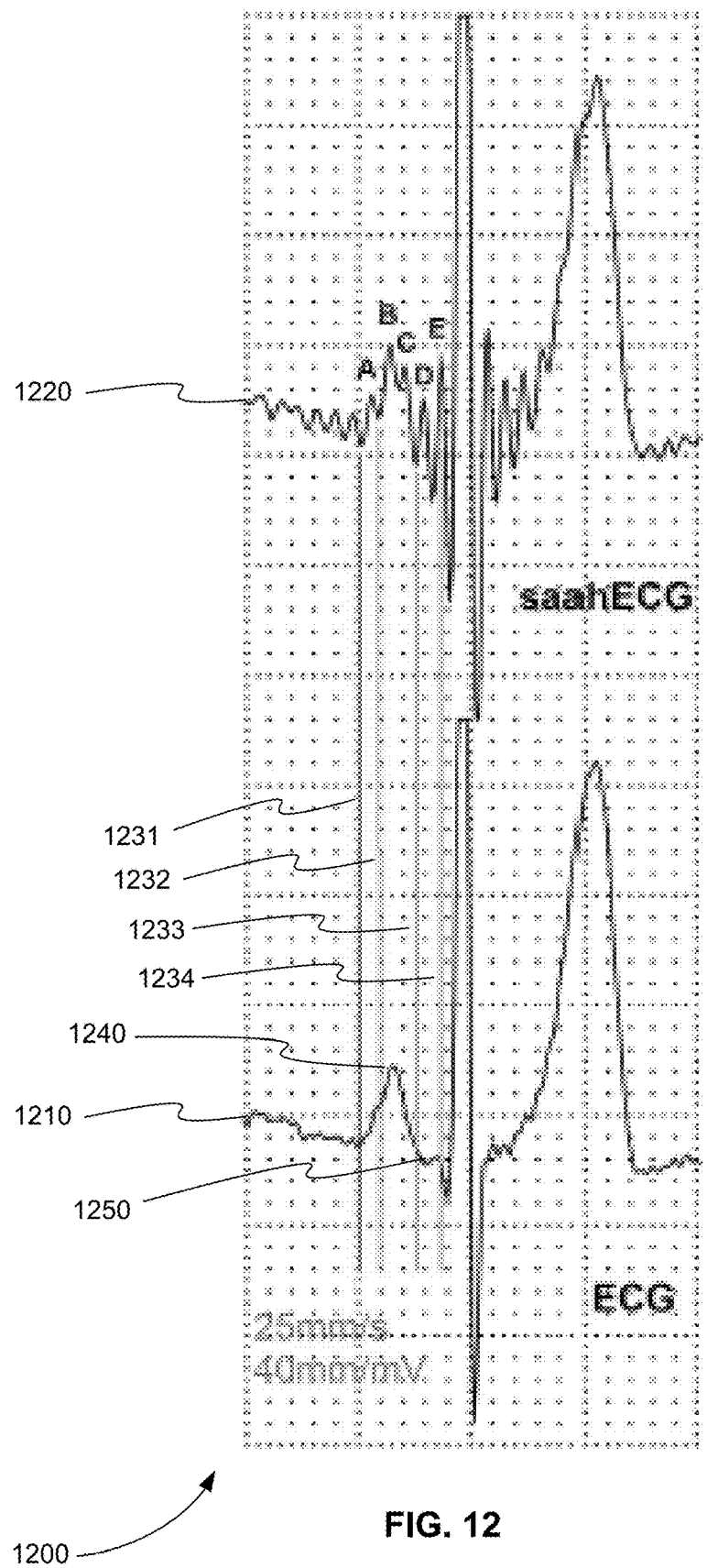
FIG. 12 is an exemplary plot of the information displayed by the saah ECG device of FIG. 10, in accordance with various embodiments.

FIG. 12 is an exemplary plot 1200 of the information displayed by the saah ECG device of FIG. 11, in accordance with various embodiments. Plot 1200 includes conventional ECG waveform 1210 and saah ECG waveform 1220. Saah ECG waveform 1220, for example, includes, among others, five subwaveforms A-E representing the depolarization of the SAN, the RA and LA, the AVN, the HIS, and the BB, respectively.

Plot 1200 also shows new data or timing information about the subwaveforms and their relation to the conventional P, Q, R, S, T, U, and J waveforms. For example, the time interval between line 1231 and line 1232 relates subwaveform A of saah ECG waveform 1220 to P waveform 1240 of conventional ECG waveform 1210. The time interval between line 1232 and line 1233 relates subwaveforms B and C of saah ECG waveform 1220 to P waveform 1240 conventional ECG waveform 1210. The time interval between line 1233 and line 1234 relates subwaveforms D and E of saah ECG waveform 1220 to PR segment 1250 conventional ECG waveform 1210.

Figure 13:
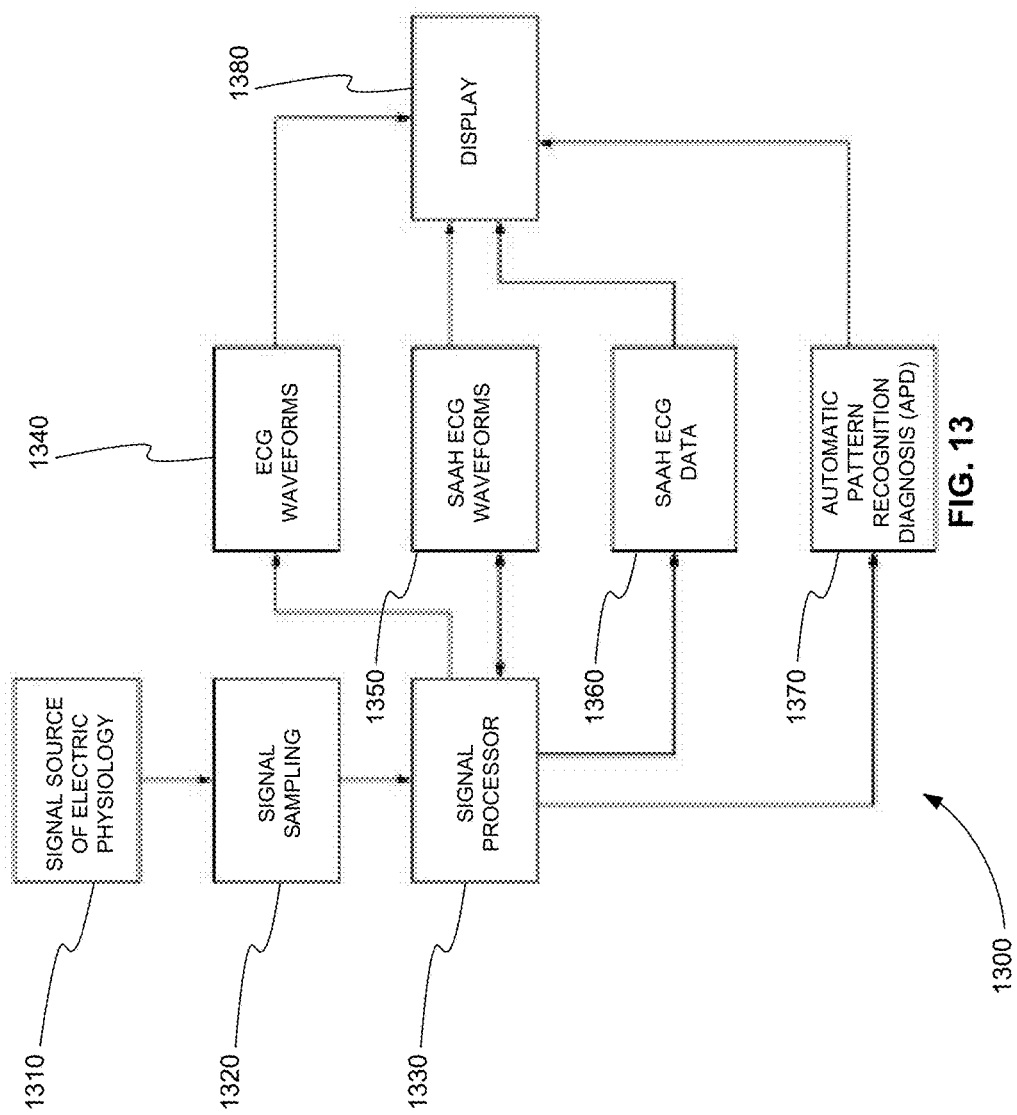
FIG. 13 is an exemplary block diagram of a saah ECG device that displays conventional ECG waveforms, saah ECG waveforms, saah ECG data, and saah ECG automatic pattern recognition diagnosis information, in accordance with various embodiments.

FIG. 13 is an exemplary block diagram 1300 of a saah ECG device that displays conventional ECG waveforms, saah ECG waveforms, saah ECG data, and saah ECG automatic pattern recognition diagnosis information, in accordance with various embodiments. In block 1310, patient heart signals are obtained. These heart signals can be obtained through noninvasive electrodes placed on the skin, such as electrodes 810 shown in FIG. 8. In various embodiments, heart signals may also be obtained using invasive electrodes placed directly on the heart. In block 1320, the heart signals are sampled or detected using a detector. The heart signals may also be amplified.

In block 1330, the sampled heart signals are processed using a signal processor. The signal processor produces four different types of information from the sampled heart signals. As shown in block 1340, the signal processor produces conventional ECG waveforms including the conventional P, Q, R, S, T, U, and J waveforms and sends them to display 1380. As shown in block 1350, the signal processor produces saah ECG waveforms. These saah ECG waveforms include subwaveforms of the conventional P, Q, R, S, T, U, and J waveforms and the intervals between them. Note that the arrow between blocks 1330 and 1350 show information following in both directions. This shows that information from the saah ECG waveforms is further analyzed by the signal processor.

As shown in block 1360, the signal processor further analyzes the saah ECG waveforms to produce saah ECG data. This saah ECG data is sent to display 1380. Additionally, as shown in block 1370, the signal processor further analyzes the saah to obtain endocardium and epicardium data. This data is compared to recorded normal and abnormal data. The signal processor then produces automatic pattern recognition diagnosis (APD) information, and this information is sent to display 1380. APD information is, for example, patterns and/or colors that allow a user to easily and quickly determine that normal or abnormal endocardium and/or epicardium data was found.

Systems and methods for detecting ECG subwaveforms are described in U.S. Pat. No. 9,339,204, which is incorporated by reference in its entirety.

System for Detecting ECG Subwaveforms

In various embodiments, an electrocardiography (ECG) system for detecting one or more subwaveforms within the P, Q, R, S, T, U, and J waveforms or in an interval between the P, Q, R, S, T, U, and J waveforms is provided. Returning to FIG. 8, the ECG system includes two or more electrodes 810, a detector 820, a signal processor 830, and a display device 840.

Two or more electrodes 810 are placed near a beating heart and receive electrical impulses from the beating heart. Two or more electrodes 810 are shown in FIG. 8 as noninvasive electrodes that are attached to the skin of a patient. In various embodiments, two or more electrodes 810 can be invasive electrodes placed directly on or within heart tissue.

Detector 820 is electrically connected to two or more electrodes 810. Detector 820 detects the electrical impulses from at least one pair of electrodes of the two or more electrodes 810. Detector 820 converts the electrical impulses to an ECG waveform for each heartbeat of the beating heart. Detector 820, for example, samples the electrical impulses. In various embodiments, detector 820 further amplifies the ECG waveform. In various embodiments, detector 820 further performs analog to digital (A/D) conversion on the ECG waveform. In various embodiments, detector 820 provides an ECG waveform with a higher signal-to-noise (S/N) ratio than conventional ECG devices.

Signal processor 830 is electrically connected to detector 820. Signal processor 830 receives the ECG waveform from detector 820. Signal processor 830 detects or calculates one or more subwaveforms within P, Q, R, S, T, U, and J waveforms of the ECG waveform or in an interval between the P, Q, R, S, T, U, and J waveforms that represent the depolarization or repolarization of anatomically distinct portions of muscle tissue of the beating heart. Signal processor 830 produces a processed ECG waveform that includes the one or more subwaveforms for each heartbeat.

Signal processor 830 can be a separate device, can be software running on a device of detector 820 or display device 840, or can be software running on a remote server and communicating with detector 820 and display device 840 through one or more communication devices. Signal processor 830 can be a separate device that includes, but is not limited to, an application specific integrated circuit (ASIC) or a field programmable gate array (FPGA) or a general purpose processor. A general purpose processor can include, but is not limited to, a microprocessor, a microcontroller, or a computer such as the system shown in FIG. 1. Signal processor 830 can be software implemented on another processor of the ECG device, such as a processor of display device 840. Signal processor 830 can also be a remote server that receives the detected and amplified difference voltage signal from detector 820, detects or calculates one or more subwaveforms within and/or in the interval between the P, Q, R, S, T, U, and J waveforms, and sends the detected and amplified different voltage signal and the one or more subwaveforms to display device 840.

Display device 840 receives the processed ECG waveform for each heartbeat and displays the processed ECG waveform for each heartbeat. The processed ECG waveform is called a saah ECG waveform, for example. As described above, display device 840 can be an electronic display device including, but not limited to, a cathode ray tube (CRT) device, light emitting diode (LED) device, or Liquid crystal display (LCD) device. Display device 840 can also be a printer device or any combination of an electronic display device and a printer. Additionally, display device 840 can include a memory device to record saah ECG waveforms, saah ECG data and conventional ECG waveforms and data. The memory device can be, but is not limited to, a volatile electronic memory, such as random access memory (RAM), a non-volatile electronic memory, such as electrically erasable programmable read-only memo (EEPROM or Flash memory), or a magnetic hard drive.

In various embodiments, the detected one or more subwaveforms include at least one subwaveform representing depolarization of the sinoatrial node (SAN), the atria (right atrium (RA) and left atrium (LA)), the atrioventricular node (AVN), the bundle of His (HIS), or the bundle branches (BB) of the beating heart.

In various embodiments, the display device 840 further displays the ECG waveform for comparison with the processed ECG waveform.

In various embodiments, signal processor 830 further calculates timing information about the one or more subwaveforms, timing information about the intervals between the one or more subwaveforms, and timing information about the one or more subwaveforms and their relation to the P, Q, R, S, T, U, and J waveforms of the ECG waveform for each heartbeat. Display device 840 further receives this timing information from signal processor 830. Display device 840 displays the timing information about the one or more subwaveforms, the timing information about the intervals between the one or more subwaveforms, and the timing information about the one or more subwaveforms and their relation to the P, Q, R, S, T, U, and J waveforms of the ECG waveform for each heartbeat.

In various embodiments, the ECG system further includes a memory device (not shown). The memory device receives the ECG waveform and the processed ECG waveform from the signal processor.

In various embodiments, the memory device further includes normally processed ECG waveform data. Normally processed ECG waveform data is stored on the memory device using signal processor 830 or a general-purpose processor (not shown). Signal processor 830 further compares the processed ECG waveform to the normally processed ECG waveform data and calculates a status condition based on the comparison. The status conditions are, for example, normal, suspicious, or abnormal.

In various embodiments, the ECG system includes a second display device (not shown) surrounding a rotating button (not shown). Signal processor 830 further sends a colored pattern to the second display device based on the status condition. The second display device provides automatic pattern recognition diagnosis (APD).

Method for Detecting ECG Subwaveforms

Figure 16:
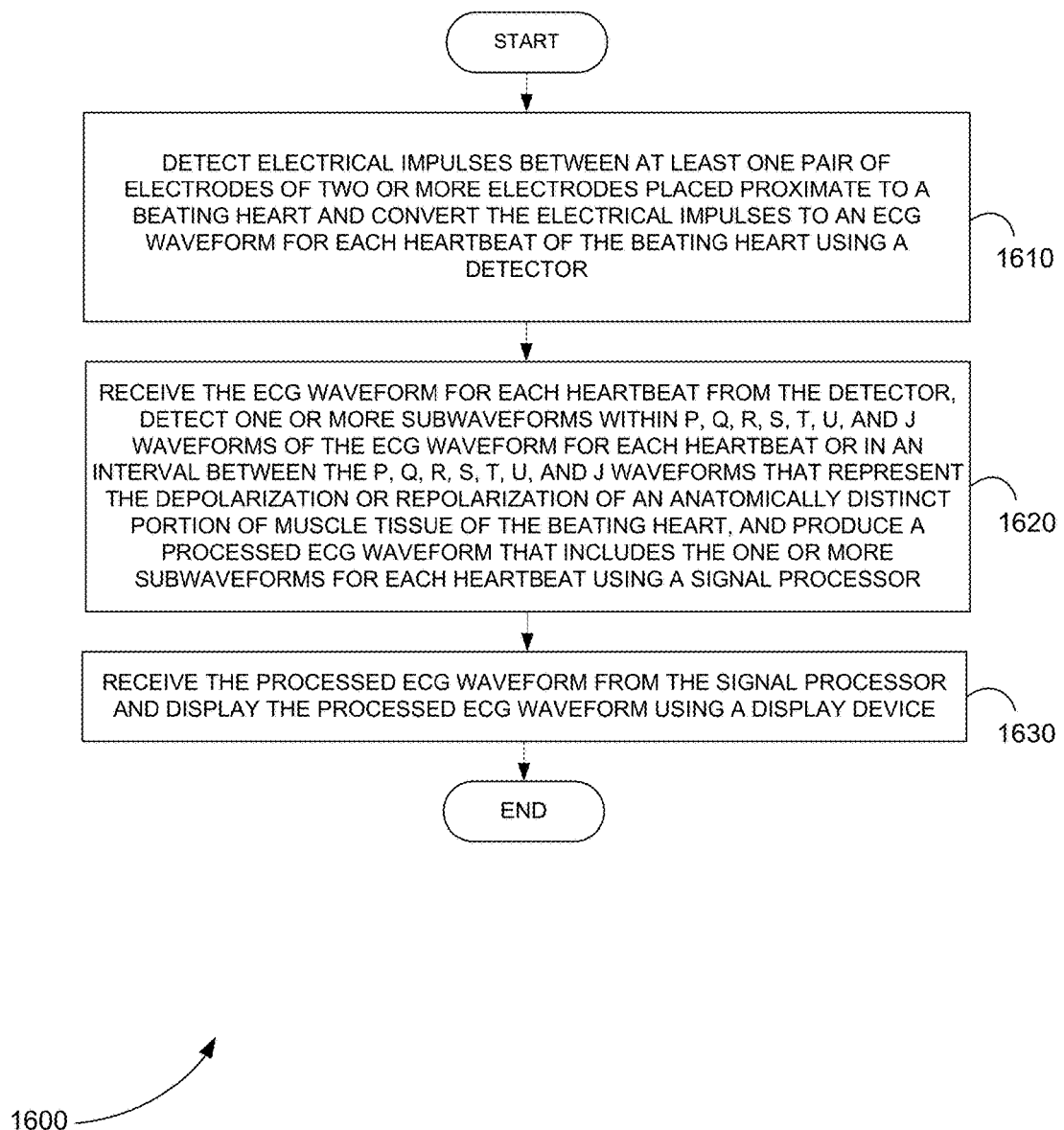
FIG. 16 is a flowchart showing a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 16 is a flowchart showing a method 1600 for detecting subwaveforms within the P, Q, R, S, T, U, and J waveforms of an ECG waveform of a heartbeat or in an interval between the P, Q, R, S, T, U, and J waveforms, in accordance with various embodiments.

In step 1610 of method 1600, electrical impulses are detected between at least one pair of electrodes of two or more electrodes placed proximate to a beating heart using a detector. The electrical impulses are converted to an ECG waveform for each heartbeat of the beating heart using the detector.

In step 1620, the ECG waveform for each heartbeat is received from the detector using a signal processor. One or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart are detected using the signal processor. A processed ECG waveform that includes the one or more subwaveforms for each heartbeat is produced using the signal processor.

In step 1630, the processed ECG waveform is received from the signal processor and the processed ECG waveform is displayed using a display device.

Computer Program Product for Detecting ECG Subwaveforms

In various embodiments, computer program products include a tangible computer-readable storage medium whose contents include a program with instructions being executed on a processor so as to perform a method for detecting subwaveforms within the P, Q, R, S, T, U, and J waveforms of an ECG waveform of a heartbeat or in an interval between the P, Q, R, S, T, U, and J waveforms. This method is performed by a system that includes one or more distinct software modules.

Figure 17:
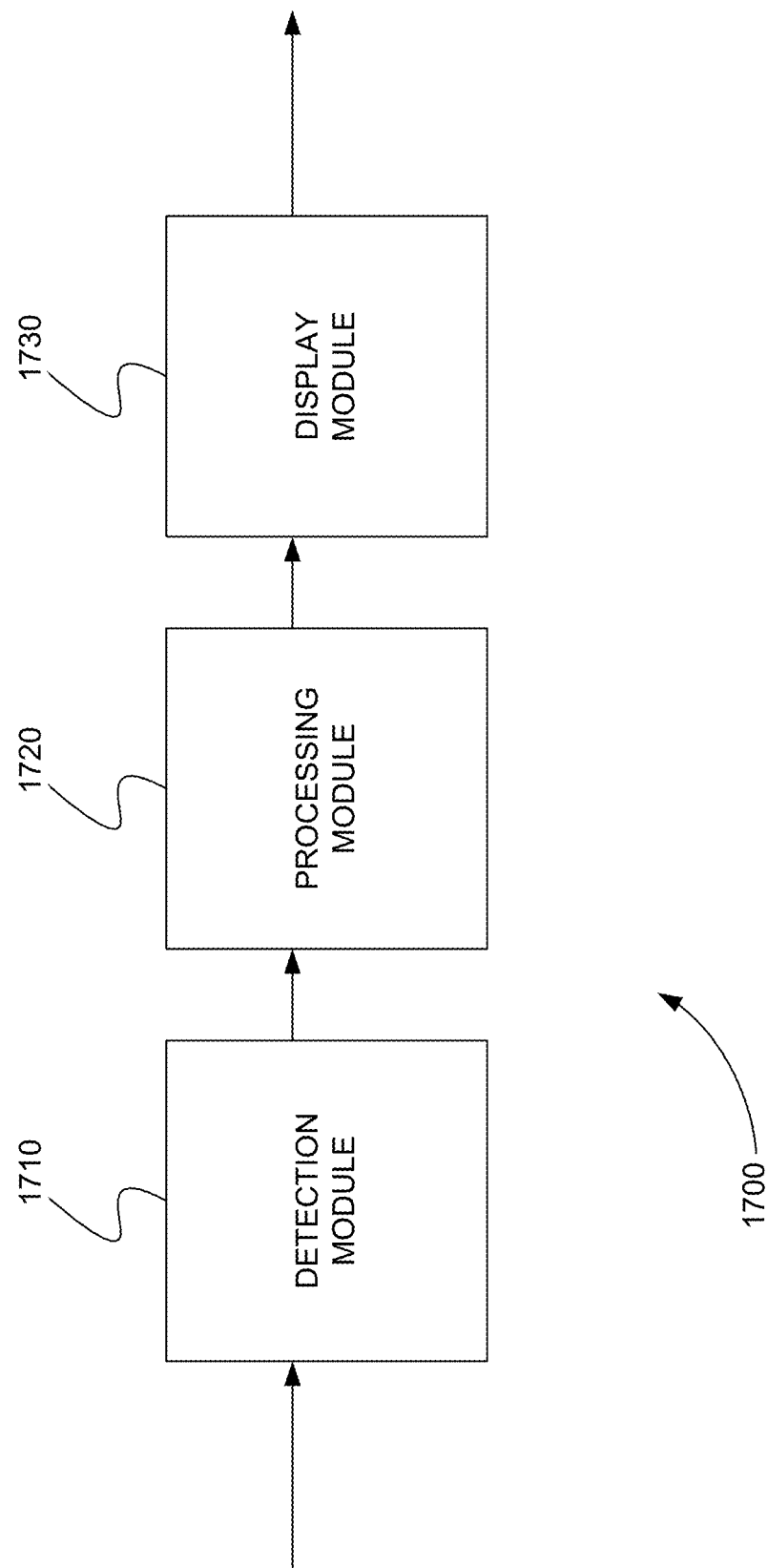
FIG. 17 is a schematic diagram of a system that includes one or more distinct software modules that performs a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 17 is a schematic diagram of a system 1700 that includes one or more distinct software modules that perform a method for detecting subwaveforms within the P, Q, R, S, T, U, and J waveforms of an ECG waveform of a heartbeat or in an interval between the P, Q, R, S, T, U, and J waveforms, in accordance with various embodiments. System 1700 includes detection module 1710, processing module 1720, and display module 1730.

Detection module 1710 detects electrical impulses between at least one pair of electrodes of two or more electrodes placed proximate to a beating heart. Detection module 1710 converts the electrical impulses to an ECG waveform for each heartbeat of the beating heart.

Processing module 1720 receives the ECG waveform for each heartbeat. Processing module 1720 detects one or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart. Processing module 1720 produces a processed ECG waveform that includes the one or more subwaveforms for each heartbeat.

Display module 1730 receives the processed ECG waveform. Display module 1730 displays the processed ECG waveform.

Multi-Domain ECG

The heart muscle, like other muscles, is activated by biologically generated electrical signals. Electrocardiography (ECG or EKG) has long been used to measure and record these electrical signals. Essentially, in ECG the electrical activity of the heart is measured from a number of different points on the body and plotted over time. As a result, ECG traces out each cardiac cycle or heartbeat as a voltage versus time waveform.

A human heart has two functional systems. The first system, referred to as a self-conduction system, is part of the atrium (including left and right atria). In a traditional ECG, the self-conduction system is represented by the P wave or PR interval. The excitation, rhythm, and conduction of every beat are completed by the collaboration of all parts of the heart, which is an axis system, including: sinoatrial node (SAN)—atrial—atrioventricular node (AVN)—Bundle of His—Bundle Branches (left and right). The Bundle of His is a collection of heart muscle cells specialized for electrical conduction that transmits the electrical impulses from the AVN to the point of the apex of the fascicular branches. Complex arrhythmias disease typically occurs in these different areas. However, ECG is only half of a sine wave.

The second system, referred to as a cardiac work system, is a pump system (one for each complete contraction and relaxation of the heart), which is done by the heart muscles. The main part of the second system is the left ventricle. In the traditional ECG, it is represented by the T wave or QT interval. There are about 10 million ventricular myocardial cells, without nerves or tracts.

Features or waves of each heartbeat waveform have been known for more than a century to correspond to electrical signals activating various parts of the heart. For example, the P wave is known to result from an electrical signal directed from the SAN to the AV node activating the atrium of the heart, to the Bundle of His to the left and right Bundle Branches, and the wave is known to result from a recovery electrical signal (ventricular depolarization and repolarization) sent to the ventricles of the heart after they have contracted. As a result, physicians are able to diagnose specific heart problems by analyzing the shapes and time of these waves.

It is thought that an ECG heartbeat waveform includes much more information about the anatomy of the heart that is not being used (scanning and displaying). In particular, it is thought that at least some of the waves in an ECG heartbeat waveform include subwaveforms that provide more detailed information about parts of the heart, as described above. Consequently, there is a need for systems and methods for processing biological electrical signals, such as signals read by ECG, in order to provide additional information about anatomical structures.

Also, electrocardiogram information itself contains a lot of information that has not been discovered so far, leaving numerous puzzles in a clinical application.

In various embodiments, new waveforms are created from a conventional ECG waveform. New indexes and new parameters are obtained from the new waveforms, so that it is possible to have a breakthrough in electrocardiogram diagnostics.

In various embodiments, heart signals are divided into different frequency bands, and then convolved or combined in one diagram. For example, 16 different frequency bands can be used. This procedure is based on the study of ergonomics and analysis procedures for frequently used information in cybernetics and nonlinear theory. The procedure makes use of the theory and analysis index of an "electrocardiogram multi-phase signal," and by using a new method of frequency division and dimension division, according to the display method of P, Q, R, S, T, U, and J waveforms P-QRS-T in a conventional ECG waveform. Heart diseases are also related to and/or complicated by different other diseases. Therefore, different numbers of frequency ranges are required to be displayed as a diagnostic requirement, because the frequency shifts of various diseases are different. In the multi-domain frequency division method, 8, 9, 10, 11, 12, 13, 14, 15, or 16 roots of multi-domain linear waveforms are displayed, and a total of 12 leads are individually displayed. If each lead is divided into 16 waveforms, there are totally 192 ECG waveforms, providing much more information. In various embodiments, multi-domain ECG (mdECG) can be used as a very valuable and new diagnostic technique for combined heart diseases. This technique can be applied in electrocardiograph, monitor, echocardiography, and invasive electrophysiological instrument.

Since the invention of ECG, the linear waveform shaped like a rope has been used. Its frequency response range is 0-150 Hz and all subwaveforms are convolved or combined together. However, heart signals are formed by combining different ultra-low frequency, low frequency, intermediate frequency, high frequency, and ultra-high frequency signals. Because in ECG all frequencies are convolved together, many fine, weak, and very valuable signals are usually submerged or overlapped by the high frequency; especially at ventricle (ECG at T-wave, ECG 'T' wave duration) and atrium (ECG at P-wave, ECG 'P' wave duration), and numerous signals accumulate within a very small time axis range, causing problems and confusion in the accuracy of the ECG diagnosis rate. As a result, the detection rate of ECG for acute myocardial infarction (AMI), acute coronary syndrome (ACS), coronary artery disease (CAD), myocardial infarction (MI), heart failure (HF) etc., with the highest incidence of cardiovascular disease is only 17%-25%. Based on a large number of research reports, for the CAD/MI/ACS patient, ECG begins to change only after ischemia reaches 70%, and only about half of the electrocardiograms show abnormality. There are 7 billion people in the world, and the percentage of people who die of cardiovascular diseases or complicated cardiovascular diseases is about 42.86% (3/7). Electrocardiogram is the most fundamental clinical assessment instrument, and it is simple, fast and economical. Therefore, it is important to improve the clinical ECG diagnosis rate, which is possible only by improving the waveform display rate of ECG.

In various embodiments, systems and methods improve the waveform display rate of ECG and clinical diagnosis rate using a 16 linear multi-domain electrocardiogram. Because the heart signals are separated according to different frequency bands with frequency bands being recombined, many high frequency signals, ultra-high frequency signal, low frequency signals, and ultra-low frequency signals are displayed with the raw heart signals at different frequency band according to the heart transduction pathway and electrophysiological rule, without the electrocardiogram being altered, i.e., at X-transverse axis and Y-vertical axis of P-QRS-T. Because the frequency bands of ECG are combined signals, mdECG separates the signals, i.e., separates them into independent waveforms consisting of different frequency bands. In this way, those frequency bands with the one linear waveform invisible and obscure in traditional ECG can be displayed clearly with different frequency bands one by one, assisting the doctor in reading, analyzing, judging and basic clinical assessment.

Figure 18:
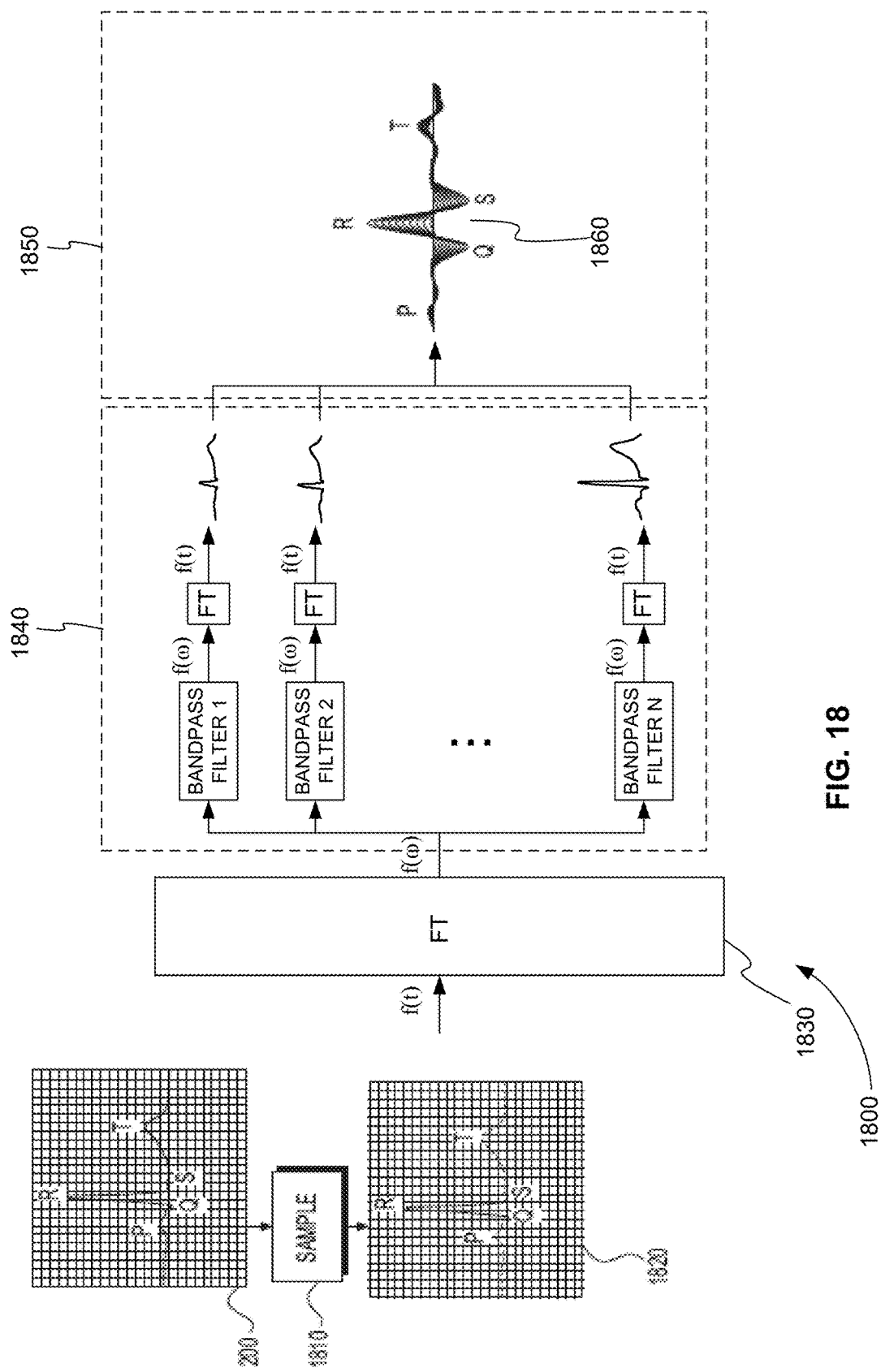
FIG. 18 is an exemplary block diagram showing a system for performing multi-domain ECG using 16 different frequency bands or domains, in accordance with various embodiments.

FIG. 18 is an exemplary block diagram 1800 showing a system for performing multi-domain ECG using 16 different frequency bands or domains, in accordance with various embodiments. Sampling block 1810 samples the electrical impulses at one electrode for one heartbeat, for example. This is shown graphically in Figure 1800 by converting ECG waveform 200 to sampled ECG waveform 1820 using block 1810. The electrical impulses for the entire ECG waveform 200 are sampled using electrodes 810 and detector 820 of FIG. 8, for example. Detector 820 of FIG. 8 can also amplify and convert the analog signal into a digital signal for digital processing.

The signal processing can be performed directly on the time domain signal received from a detector or the time domain signal received from a detector can be converted to the frequency domain for algorithmic processing. In FIG. 18, block 1830 converts sampled ECG waveform 1820 to a frequency domain signal. The time domain signal is converted into a frequency domain signal using a Fourier transform, for example.

As described above, through animal and/or human experimentation, the frequency bands associated with different muscles of the heart can be determined. The frequency bands used here can be based on those bands determined experimentally, for example. Alternatively, the 16 frequency bands can be found by dividing the total frequency bands 16 ways. The different band can have the same bandwidth or can have different bandwidths.

In block 1840, 16 different band pass filters filter sampled ECG waveform 1820's frequency domain signal into 16 different frequency domain signal. These 16 different 16 different frequency domain signals are then converted back to the time domain. The result of block 1840 is 16 different time domain signals.

In block 1850, the 16 different time domain signals are combined or plotted together in the time domain as one multi-domain ECG waveform 1860. In Figure 1800, a conventional ECG signal from one electrode is processed into a multi-domain ECG waveform that includes 16 different time domain signals. In various embodiments, a conventional ECG signal from one electrode, however, can be processed into a multi-domain ECG waveform that includes any number of different time domain signals.

Figure 19:
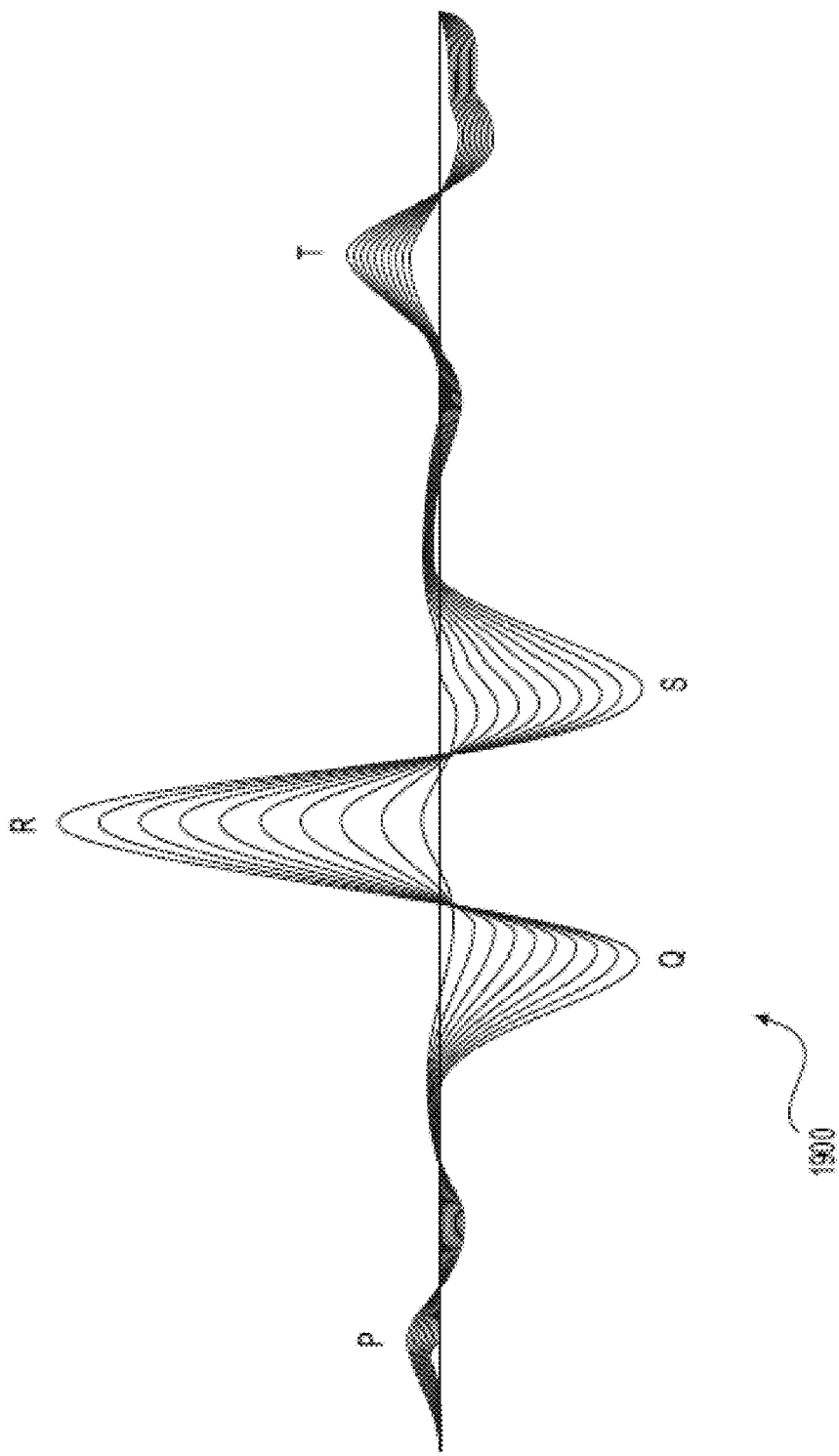
FIG. 19 is an exemplary plot of a multi-domain ECG waveform that includes 10 different time domain signals, in accordance with various embodiments.

FIG. 19 is an exemplary plot 1900 of a multi-domain ECG waveform that includes 10 different time domain signals, in accordance with various embodiments.

Figure 20:
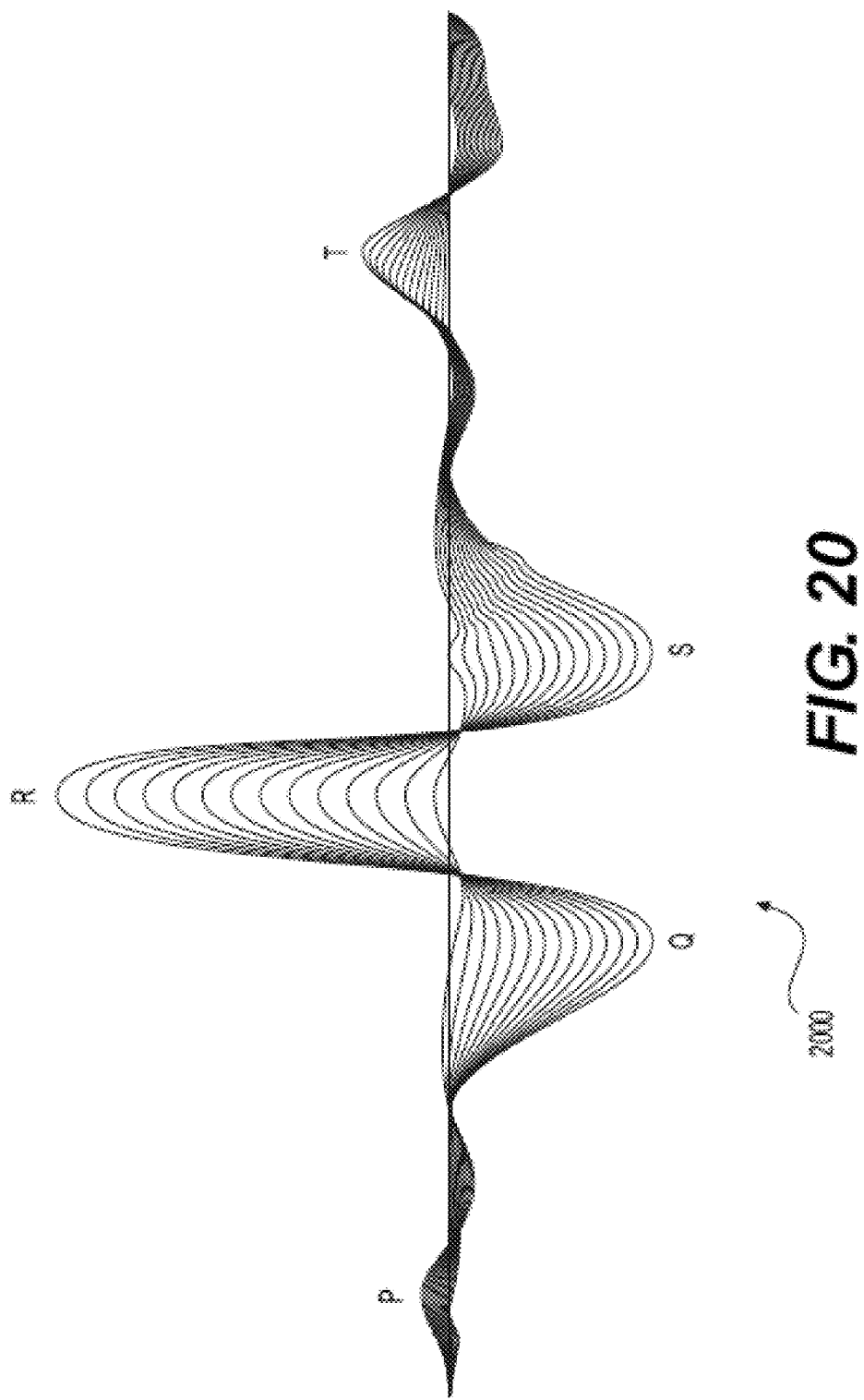
FIG. 20 is an exemplary plot of a multi-domain ECG waveform that includes 14 different time domain signals, in accordance with various embodiments.

FIG. 20 is an exemplary plot 2000 of a multi-domain ECG waveform that includes 14 different time domain signals, in accordance with various embodiments.

Figure 21:
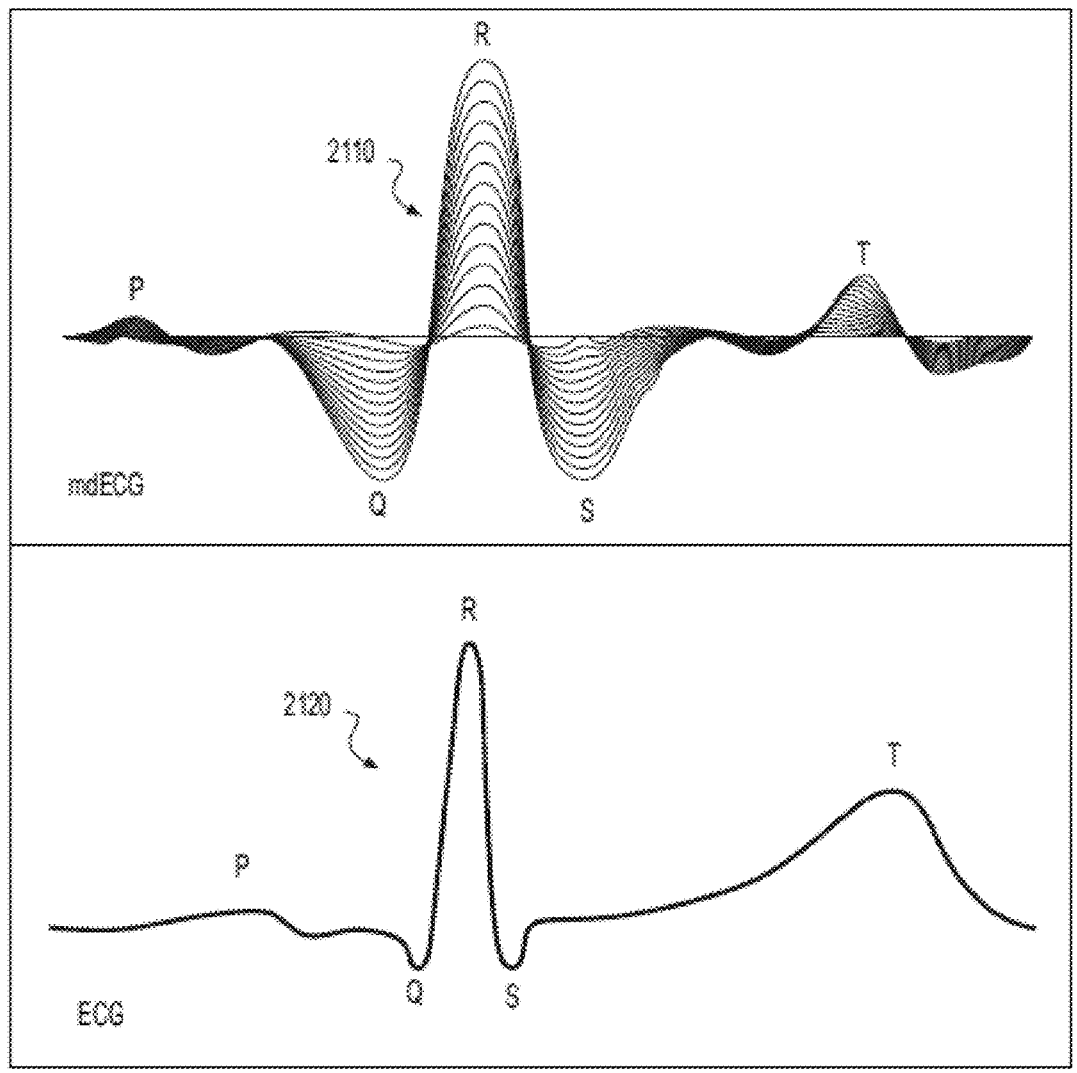
FIG. 21 is an exemplary alignment of a multi-domain ECG waveform that includes 16 different time domain signals with a conventional ECG waveform, in accordance with various embodiments.

FIG. 21 is an exemplary alignment 2100 of a multi-domain ECG waveform 2110 that includes 16 different time domain signals with a conventional ECG waveform 2120, in accordance with various embodiments. Multi-domain ECG waveform 2110 is produced from conventional ECG waveform 2120 using the system depicted in FIG. 18, for example. As shown in FIG. 21, multi-domain ECG waveform 2110 can display data with negative values while conventional ECG waveform 2120 cannot.

Systems and methods for detecting multi-domain ECG waveforms are described in U.S. Pat. No. 9,538,930, which is incorporated by reference in its entirety.

Stethoscope ECG System

As described above, recently many additional measurement functions have been added to stethoscopes including ECG. Although ECG measurement has been combined with a stethoscope in existing systems, such systems are not currently capable of advanced signal processing of ECG signals, such as processing saah ECG waveforms or multi-domain ECG waveforms. As a result, the ECG measurement provided by such systems is limited. In addition, the displays of such systems are generally small, thus limiting the amount of information that can be displayed at any one time.

As a result, improved systems and methods are needed to combine stethoscopes with ECG measurement to provide advanced signal processing of ECG signals and to provide detailed information to healthcare providers.

Figure 22:
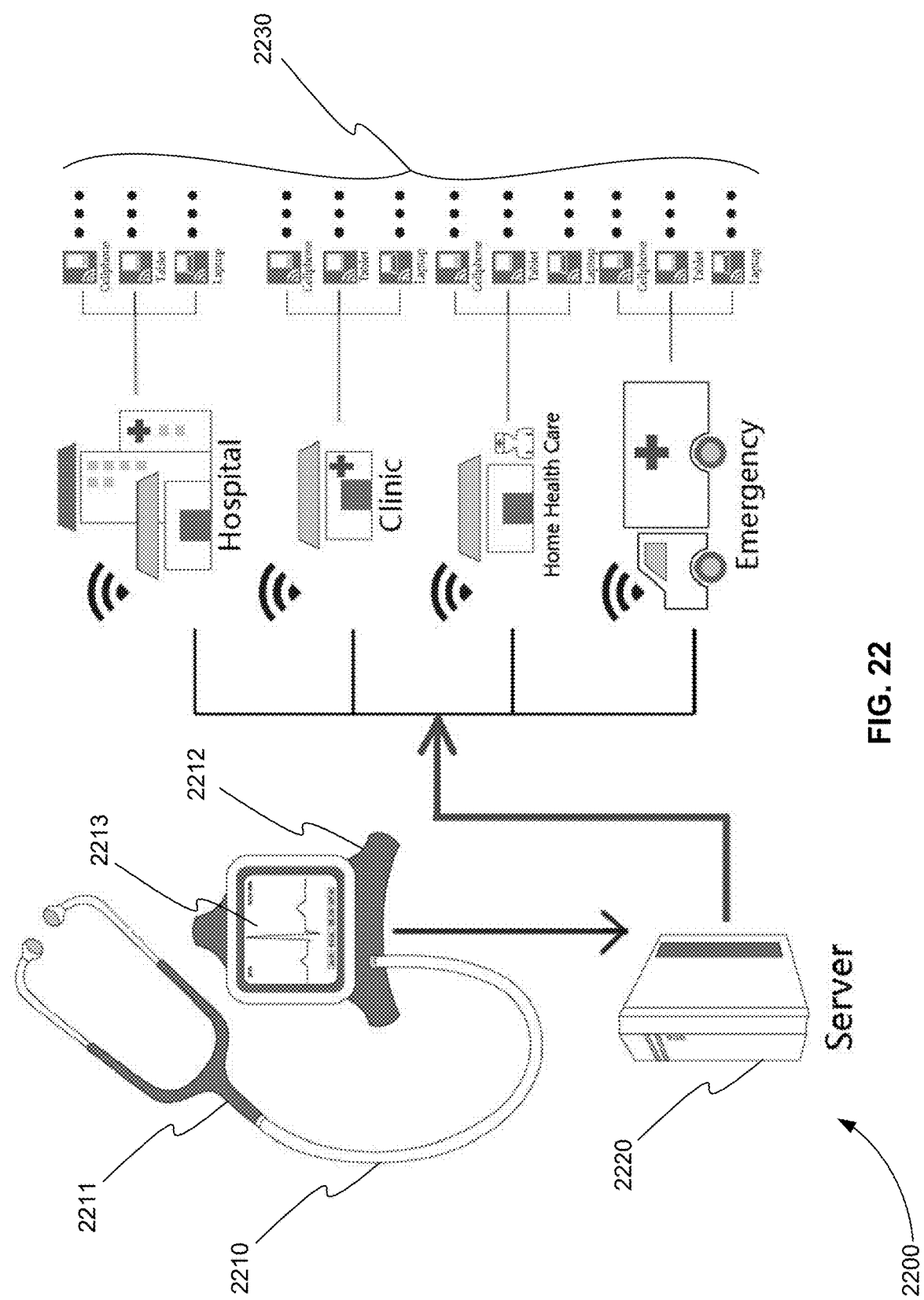
FIG. 22 is an exemplary diagram of a stethoscope ECG system, in accordance with various embodiments.

FIG. 22 is an exemplary diagram 2200 of a stethoscope ECG system, in accordance with various embodiments. The stethoscope ECG system of FIG. 22 includes electronic acoustic stethoscope 2210 and computer server 2220. Computer server 2220 is adapted or configured to allow at least one client device 2230 to access the data it receives and processes, or to transmit the data it receives and processes to at least one client device 2230.

Electronic acoustic stethoscope 2210 includes earpiece 2211 and chestpiece 2212. When chestpiece 2212 is on the chest of a patient and over the heart of the patient, it obtains heart sounds and heart electrical signals. Chestpiece 2212 is an acoustic and electronic device that is battery powered. Chestpiece 2212 conveys acoustic or electro-acoustic signals to earpiece 2211 to allow the user to hear heart sounds. Chestpiece 2212 displays heart electrical signals as a conventional ECG waveform on display 2213. A conventional ECG waveform is displayed on display 2213 to let the user know that a stable ECG waveform has been found. When a stable ECG waveform has been found, it can be sent to computer server 2220 for signal processing.

Chestpiece 2212 includes a wireless communication device (not shown). This wireless communication device allows heart sounds (a stable phonocardiogram) and/or a stable ECG waveform to be sent to computer server 2220 for signal processing either automatically or under user control. For example, once a user sees a stable ECG waveform on display 2213, they can press a button on display 2213 or chestpiece 2212 that transmits the ECG waveform to computer server 2220 for signal processing.

When computer server 2220 receives a phonocardiogram or an ECG waveform from chestpiece 2212, it processes the phonocardiogram or ECG waveform. For example, computer server 2220 can process a phonocardiogram into an image for display on at least one client device 2230. Similarly, computer server 2220 can process an ECG waveform into a saah ECG waveform or a multi-domain ECG waveform as described above for display on at least one client device 2230. Additionally, computer server 2220 can process an ECG waveform using an artificial intelligence system (AIS) that provides automatic mapping of invasive parameters P-A (pacing to atrial interval), A-H (atrial to AVN interval), and H-V (His bundle to ventricles interval). Quantitative and qualitative information provided by AIS is referred to as aiECG information. In addition to providing processed information to at least one client device 2230, computer server 2220 can transmit processed information back to display 2213 of chestpiece 2212.

Chestpiece 2212 can store a phonocardiogram or an ECG waveform and transmit it to computer server 2220 whenever a wireless signal can be obtained. The communications device of chestpiece 2212 can transmit and receive data using any wireless protocol including, but not limited to, WiFi, Bluetooth, 4G cellular, or 5G cellular protocols. For example, chestpiece 2212 can transmit a signal obtained to computer server 2200 whenever it is at or near a hospital, home healthcare facility, an operating room, an emergency room, an intensive care unit, a cardiac care unit, a neonatal intensive care unit, a surgical intensive care unit, or any other critical care facility. After processing the signal, computer server 2200 can send a traditional ECG, a processed ECG, a phonocardiogram image, invasive parameters, and other information to at least one client device 2230 specified by the user or healthcare provider using chestpiece 2212.

Figure 23:
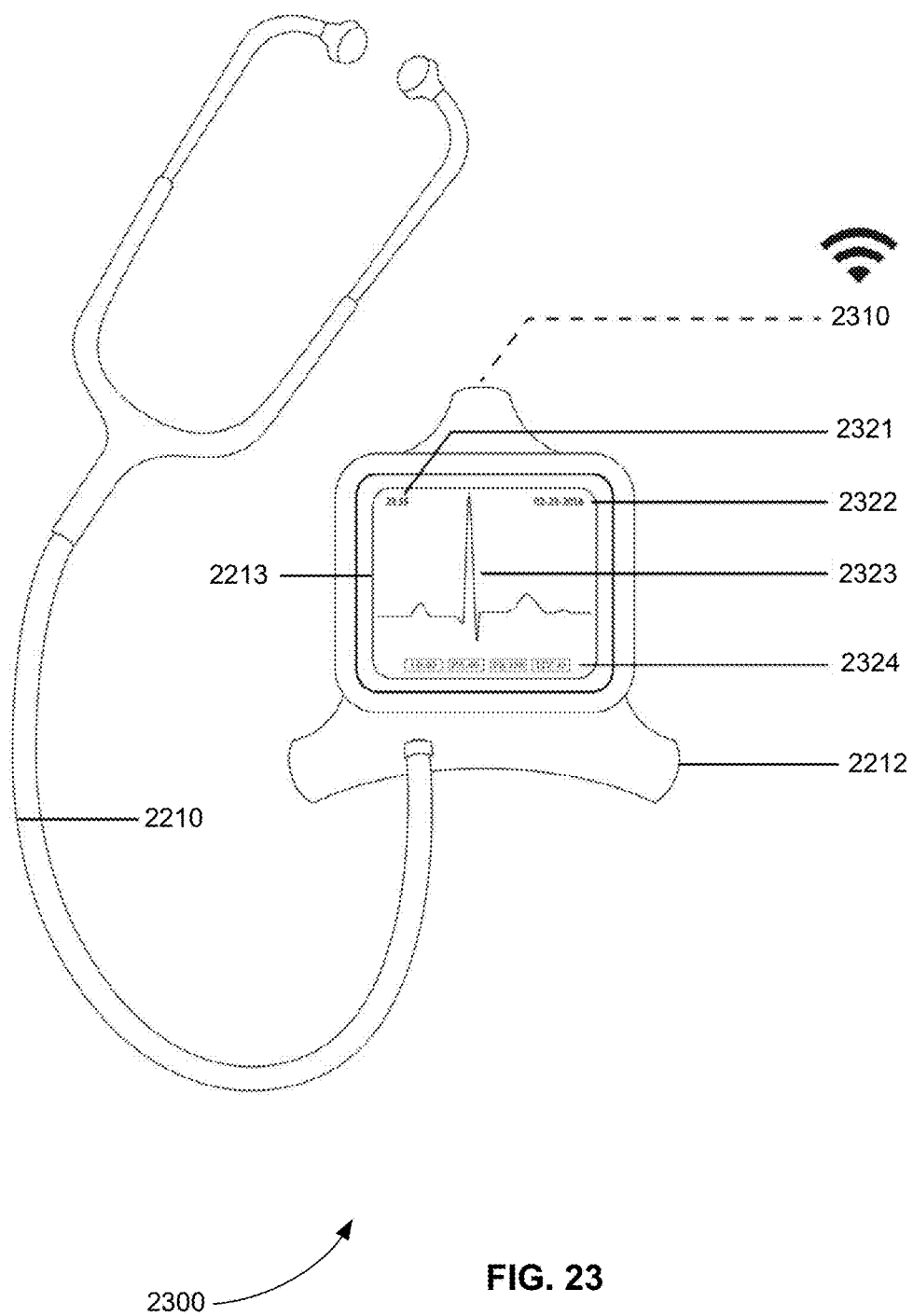
FIG. 23 is an exemplary diagram of an electronic acoustic stethoscope of a stethoscope ECG system showing the display side of the chestpiece of the electronic acoustic stethoscope, in accordance with various embodiments.

FIG. 23 is an exemplary diagram 2300 of an electronic acoustic stethoscope of a stethoscope ECG system showing the display side of the chestpiece of the electronic acoustic stethoscope, in accordance with various embodiments. Electronic acoustic stethoscope 2210 includes chestpiece 2212. Chestpiece 2212 includes wireless communications device 2310 and display 2213. Display 2213 shows time 2321, date 2322, traditional ECG waveform 2323, and invasive ECG parameters 2324.

Figure 24:
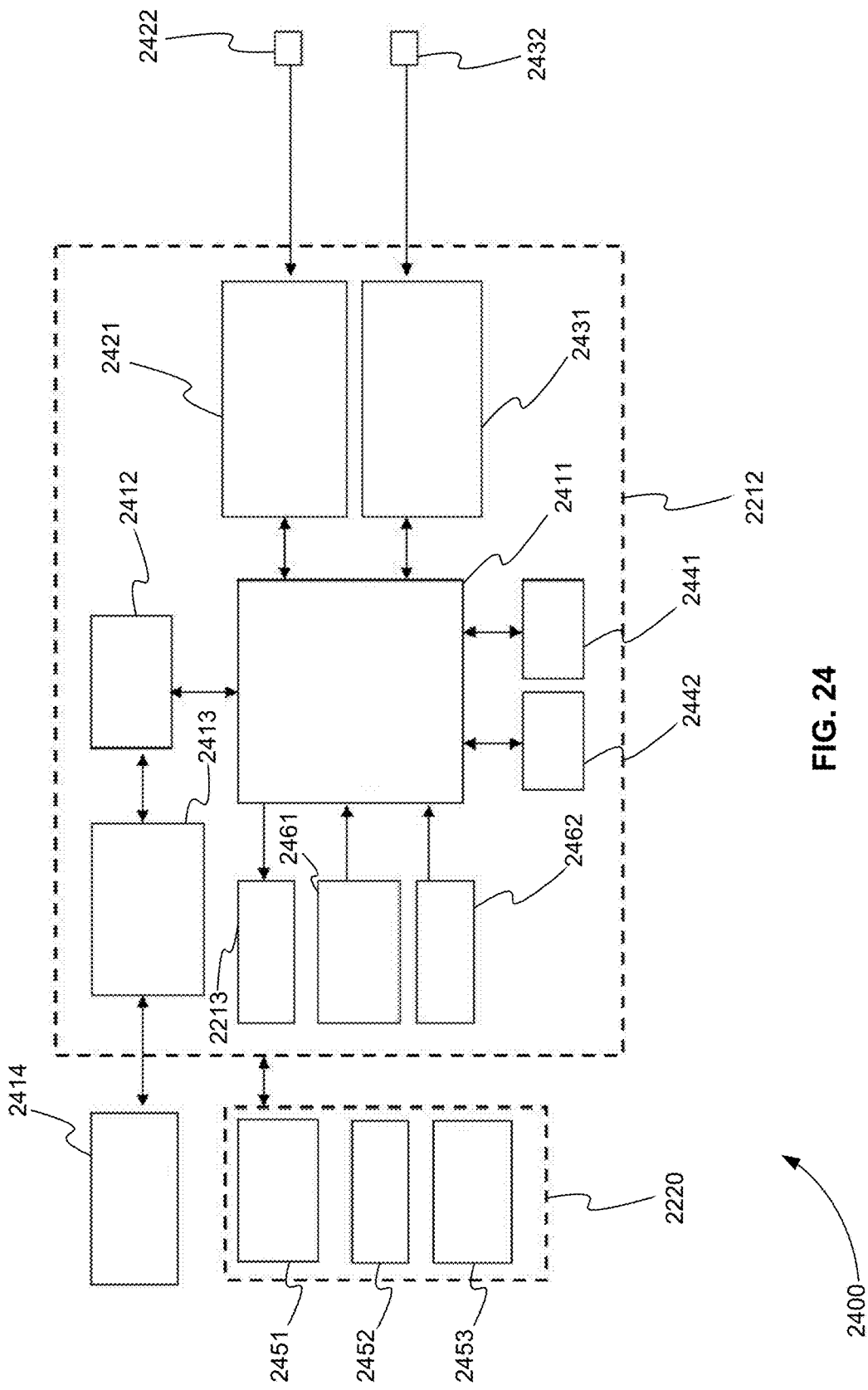
FIG. 24 is an exemplary diagram of the electronic components of a chestpiece of an electronic acoustic stethoscope, in accordance with various embodiments.

FIG. 24 is an exemplary diagram 2400 of the electronic components of a chestpiece of an electronic acoustic stethoscope, in accordance with various embodiments. Chestpiece 2212 includes a number of electronic components. Chestpiece 2212 includes main circuit board 2411, which includes custom and general processing units (GPUs), for example. Chestpiece 2212 includes battery 2412 and module 2413 for wireless charging of battery 2412. Battery 2412 can be, for example, a lithium ion battery. Module 2413 for wireless charging of battery 2412 can be electromagnetically coupled to external wireless charger 2414, for example.

Chestpiece 2212 includes module 2421 for acquisition of heart sounds or a phonocardiogram. For example, module 2421 is electrically coupled or connected to one or more microphones or piezoelectric devices 2422 of chestpiece 2212 to obtain heart sounds or a phonocardiogram. Module 2421, for example, can convert an analog signal to a digital signal.

Chestpiece 2212 also includes module 2431 for acquisition of electrical signals or an ECG waveform. For example, module 2431 is electrically coupled or connected to at least four electrodes 2432 of chestpiece 2212 or external ECG pads to obtain ECG electrical signals. Module 2432, for example, can convert analog signals to digital signals.

Chestpiece 2212 includes one or more wireless communications modules 2441 and 2442. For example, wireless communications module 2441 can be used for transmitting and receiving phonocardiograms and ECG waveforms to and from server computer 2220 using WiFi. Similarly, wireless communications module 2442 can be used for transmitting and receiving phonocardiograms and ECG waveforms to and from server computer 2220 using a 4G cellular network protocol. On server computer 2220, phonocardiograms are converted to images 2451 or traditional ECG waveforms are converted to saah ECG waveforms 2452, domain multi-domain ECG waveforms 2453, ECG parameters, or aiECG information, for example.

Finally, chestpiece 2212 includes display 2213 for displaying information to a user. Display 2213 is, for example, a liquid crystal display (LCD) device. Chestpiece 2212 can also include input devices 2461 and 2462 for receiving information from a user. Input device 2461 can be a touch screen and input device 2462 can include one or more buttons or switches, for example. Input devices 2461 and 2462 can be used to manually initiate a transmission to server computer 2220, for example.

Figure 14:
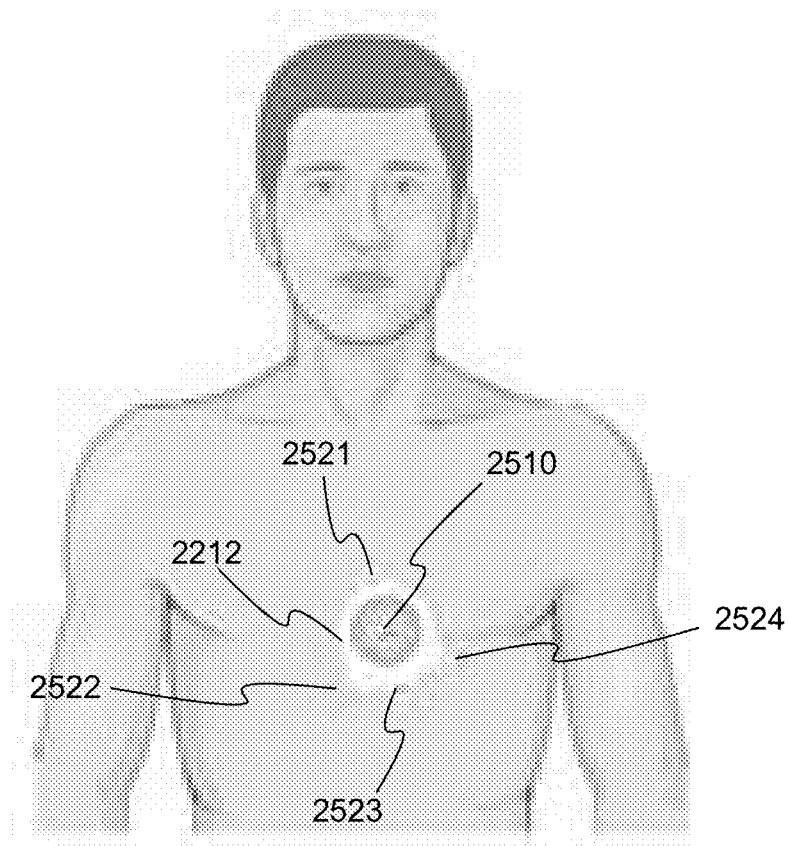
FIG. 14 is an exemplary diagram showing the placement of the measurement side of a chestpiece of an electronic acoustic stethoscope of a stethoscope ECG system on the chest of a patient, in accordance with various embodiments.

FIG. 14 is an exemplary diagram 1400 showing the placement of the measurement side of a chestpiece of an electronic acoustic stethoscope of a stethoscope ECG system on the chest of a patient, in accordance with various embodiments. Chestpiece 2212 is placed on the chest of a patient with the measurement side facing and touching the skin. The measurement side of chestpiece 2212 includes acoustic diaphragm 2510 and at least four electrodes 2521, 2522, 2523, and 2524. Note that in FIG. 14 the measurement side is shown facing up only to show the placement of acoustic diaphragm 2510 and at least four electrodes 2521, 2522, 2523, and 2524 with respect to a patient's chest.

Figure 15:
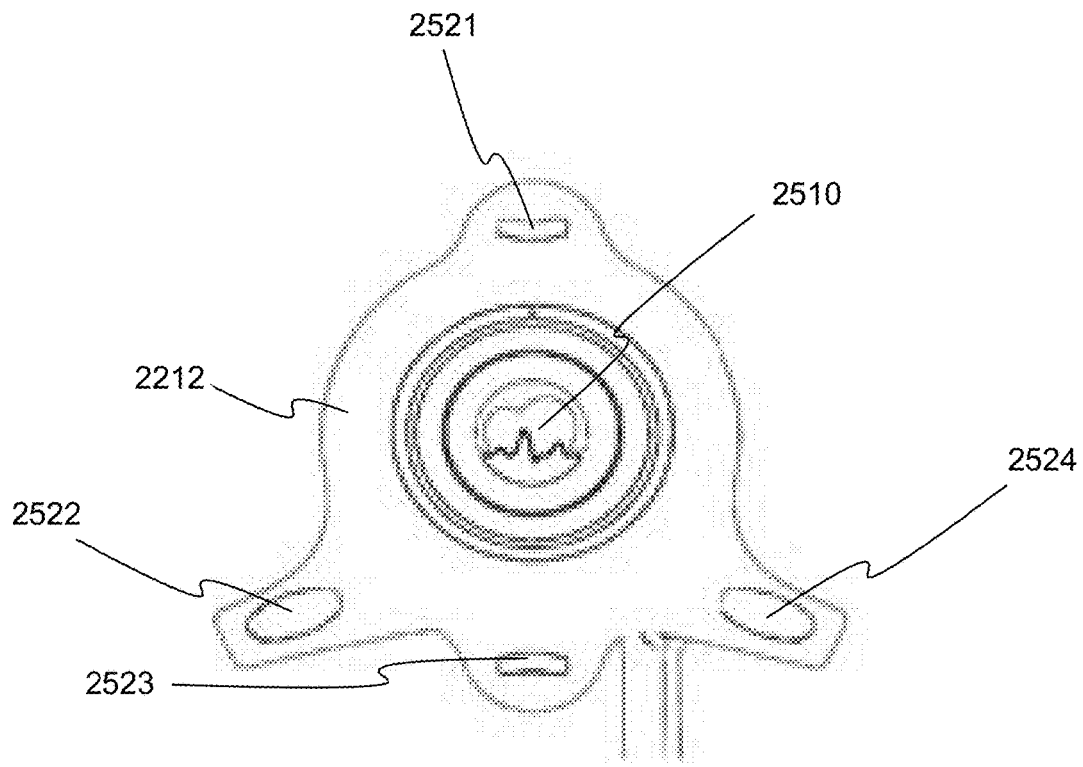
FIG. 15 is an exemplary diagram of the measurement side of a chestpiece of an electronic acoustic stethoscope of a stethoscope ECG system, in accordance with various embodiments.

FIG. 15 is an exemplary diagram 1500 of the measurement side of a chestpiece of an electronic acoustic stethoscope of a stethoscope ECG system, in accordance with various embodiments. The measurement side of chestpiece 2212 includes acoustic diaphragm 2510 and at least four electrodes 2521, 2522, 2523, and 2524. Acoustic diaphragm 2510 is designed to contact a patient's chest above the heart, receive heart sounds, and convey the heart sounds either directly to an earpiece (not shown) or indirectly to the earpiece through an amplifier and/or a transducer such as a microphone or piezoelectric device (not shown). The combination of acoustic diaphragm 2510 and an electronic transducer such as a microphone or piezoelectric device is referred to as an acoustic transducer.

Figure 25:
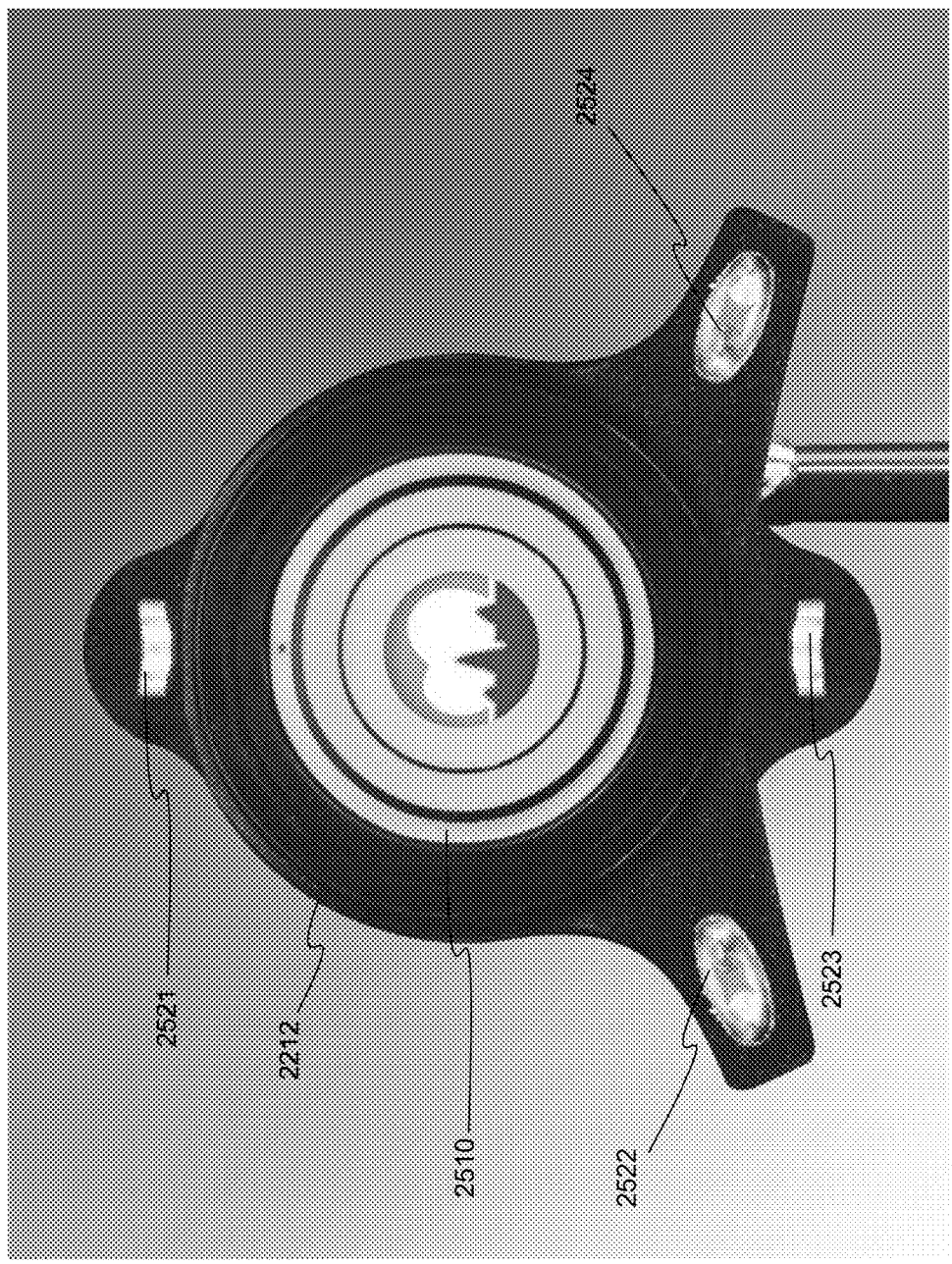
FIG. 25 is an exemplary image of the measurement side of a chestpiece of an electronic acoustic stethoscope of a stethoscope ECG system, in accordance with various embodiments.

FIG. 25 is an exemplary image 2500 of the measurement side of a chestpiece of an electronic acoustic stethoscope of a stethoscope ECG system, in accordance with various embodiments. Again, the measurement side of chestpiece 2212 includes acoustic diaphragm 2510 and at least four electrodes 2521, 2522, 2523, and 2524. At least four electrodes 2521, 2522, 2523, and 2524 are designed to contact a patient's chest above the heart, receive electrical heart signals, and convey the heart signals to the main circuit board of chestpiece 2212 for processing into a traditional ECG waveform. At least four electrodes 2521, 2522, 2523, and 2524 are located around the perimeter of chestpiece 2212 in order to surround the heart when placed on the chest and provide the necessary electrical signals for a traditional ECG waveform.

As one of ordinary skill in the art can appreciate, a traditional ECG waveform is typically made up of signals from 12 ECG leads or electrodes. These 12 ECG leads include I, II, III, aVR, aVL, aVF, V1, V2, V3, V4, V5, and V6. Even in a traditional ECG device, signals from only eight electrodes are usually measured. These eight electrodes include limb leads I and II and chest leads: V1, V2, V3, V4, V5, and V6. Limb lead III and augmented limb leads aVR, aVL, and aVF are typically calculated.

In various embodiments, at least four electrodes 2521, 2522, 2523, and 2524 are used to make measurements for limb leads I and II. All other leads are calculated. For example, for a saah ECG waveform at least four electrodes 2521, 2522, 2523, and 2524 are used to make measurements for limb leads I and II and leads III, aVR, aVL, and aVF are calculated. For an aiECG information, at least four electrodes 2521, 2522, 2523, and 2524 are used to make measurements for limb leads I and II only.

At least four electrodes 2521, 2522, 2523, and 2524 can be metal contacts made of gold or silver, for example. At least four electrodes 2521, 2522, 2523, and 2524 can alternatively be disposable pad like tabs placed on the skin after disinfecting the skin surface. There are at least two methods because certain jurisdictions or countries do not allow the reuse of electrodes from patient to patient.

For patients with a larger body surface, at least four electrodes 2521, 2522, 2523, and 2524 may have to be spread out further apart. In various embodiments, a chestpiece can include electrodes on arms that can be extended to adhere to various body types.

Figure 26:
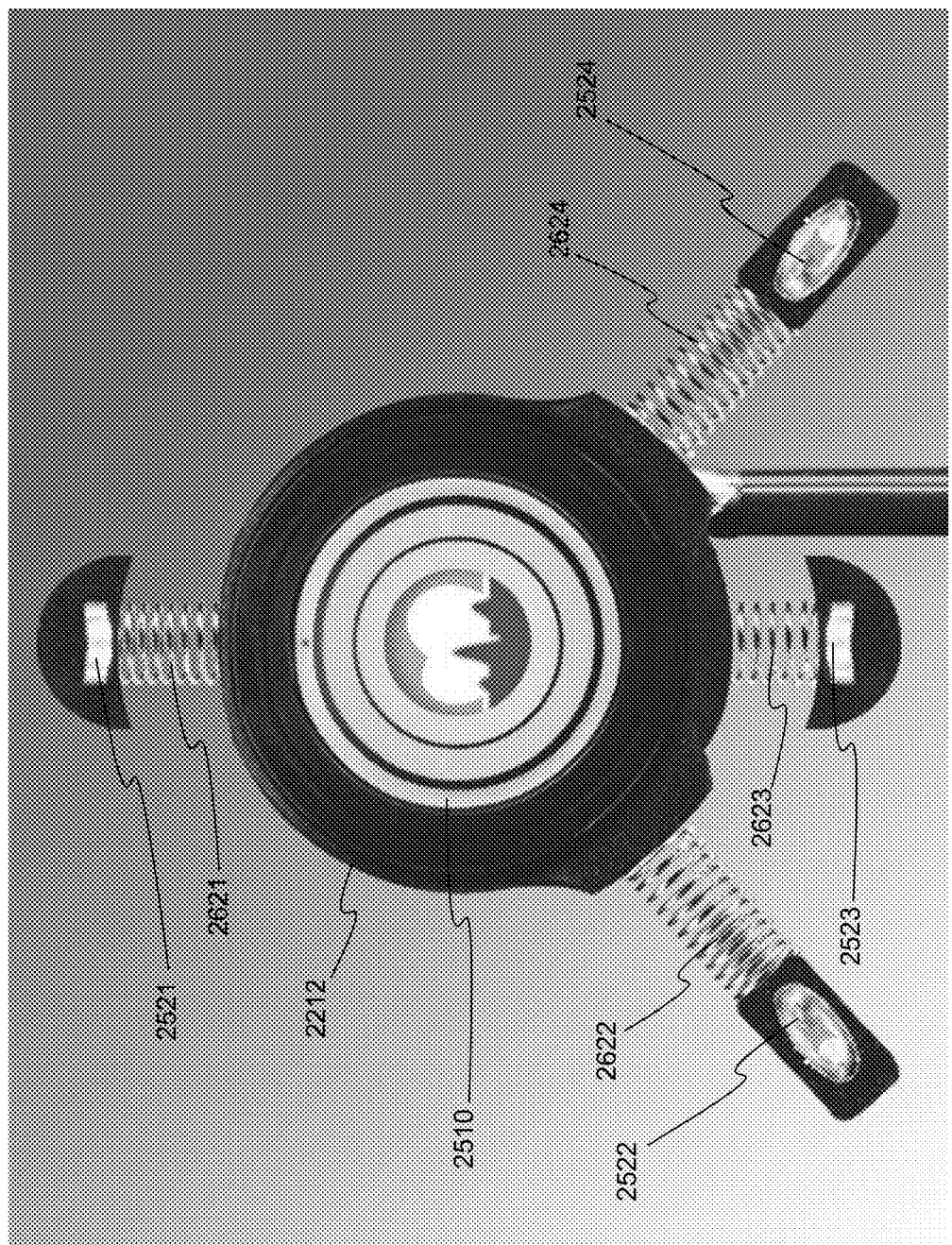
FIG. 26 is an exemplary image of the measurement side of a chestpiece of an electronic acoustic stethoscope of a stethoscope ECG system showing electrodes on extendable arms, in accordance with various embodiments.

FIG. 26 is an exemplary image 2600 of the measurement side of a chestpiece of an electronic acoustic stethoscope of a stethoscope ECG system showing electrodes on extendable arms, in accordance with various embodiments. The measurement side of chestpiece 2212 still includes acoustic diaphragm 2510 and at least four electrodes 2521, 2522, 2523, and 2524. However, at least four electrodes 2521, 2522, 2523, and 2524 are located on extendable arms 2621, 2622, 2623, and 2624, respectively. Extendable arms 2621, 2622, 2623, and 2624 are elastic extendable coils or springs, for example.

Figure 27:
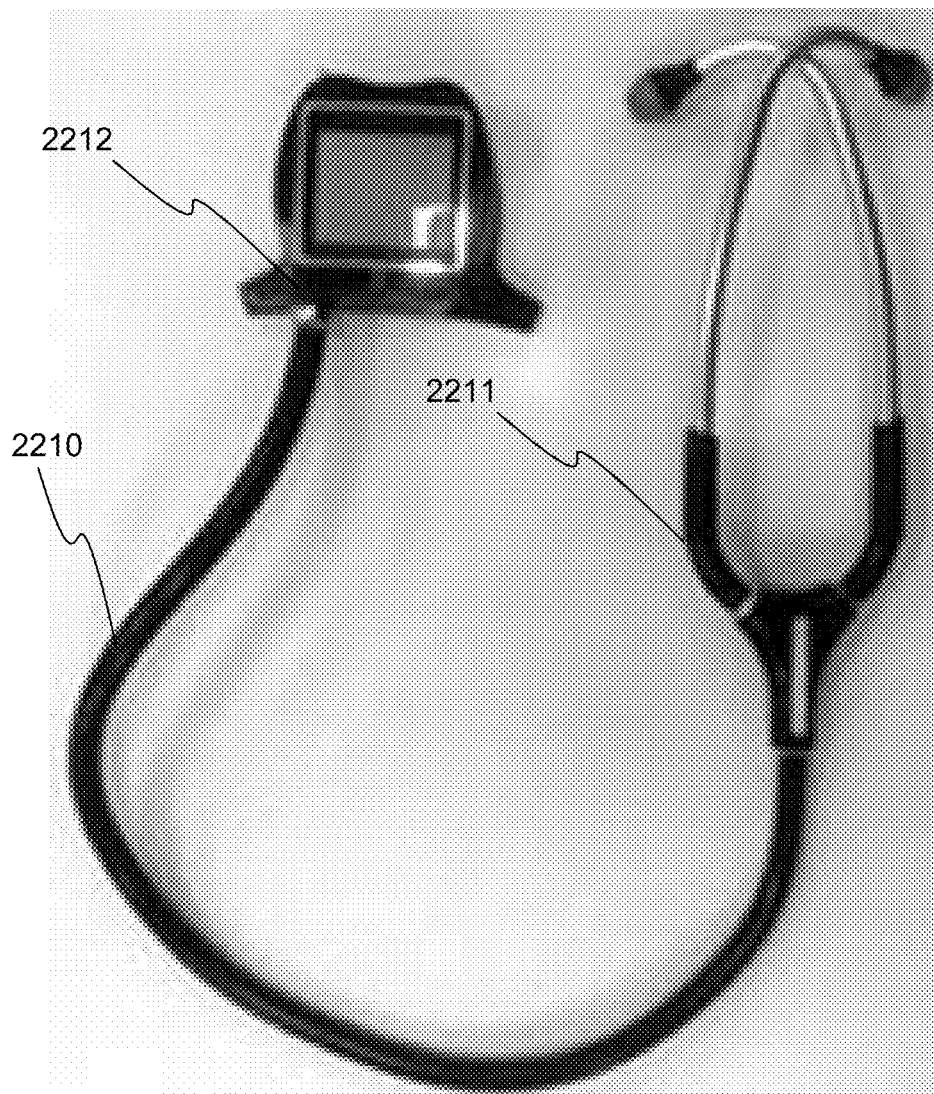
FIG. 27 is an exemplary image of an electronic acoustic stethoscope of a stethoscope ECG system, in accordance with various embodiments.

FIG. 27 is an exemplary image 2700 of an electronic acoustic stethoscope of a stethoscope ECG system, in accordance with various embodiments. Electronic acoustic stethoscope 2210 includes earpiece 2211 and chestpiece 2212.

Figure 28:
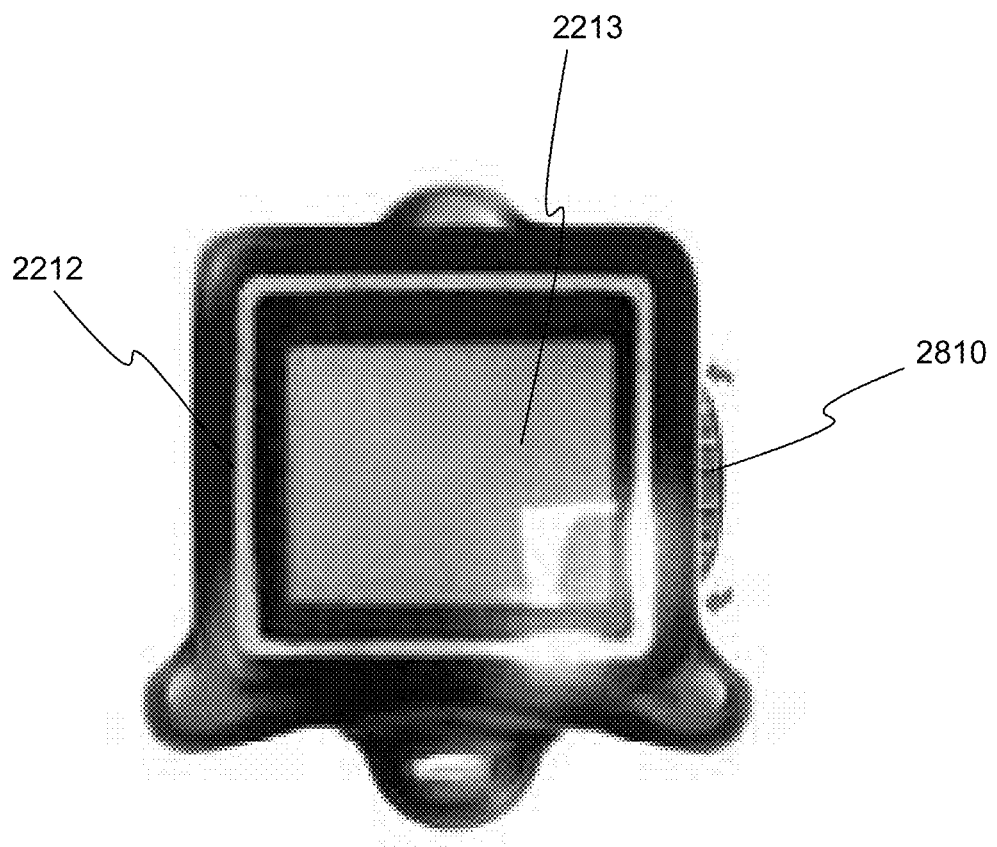
FIG. 28 is an exemplary image of the display side of a chestpiece of an electronic acoustic stethoscope of a stethoscope ECG system, in accordance with various embodiments.

FIG. 28 is an exemplary image 2800 of the display side of a chestpiece of an electronic acoustic stethoscope of a stethoscope ECG system, in accordance with various embodiments. Chestpiece 2212 includes display 2213. Chestpiece 2212 can also include pointing device or mouse wheel 2810 to allow selection and objects on display 2213.

Returning to FIG. 22 and in various embodiments, electronic acoustic stethoscope 2210 is a sampling device designed to capture a traditional ECG waveform and transmit it to computer server 2220. Computer server 2220 is then used to process the traditional ECG waveform and convert it into more informative ECG waveforms such as a saah ECG waveform, a multi-domain ECG waveform or an aiECG information. aiECG information waveform includes timing intervals or parameters such as PA, AH, HV, and PR intervals. Computer server 2220 is adapted or configured to allow at least one client device 2230 to access the ECG waveforms it receives and processes, or to transmit the ECG waveforms it receives and processes to at least one client device 2230. At least one client device 2230 is needed to display the more informative ECG waveforms because they include much more information.

Figure 29:
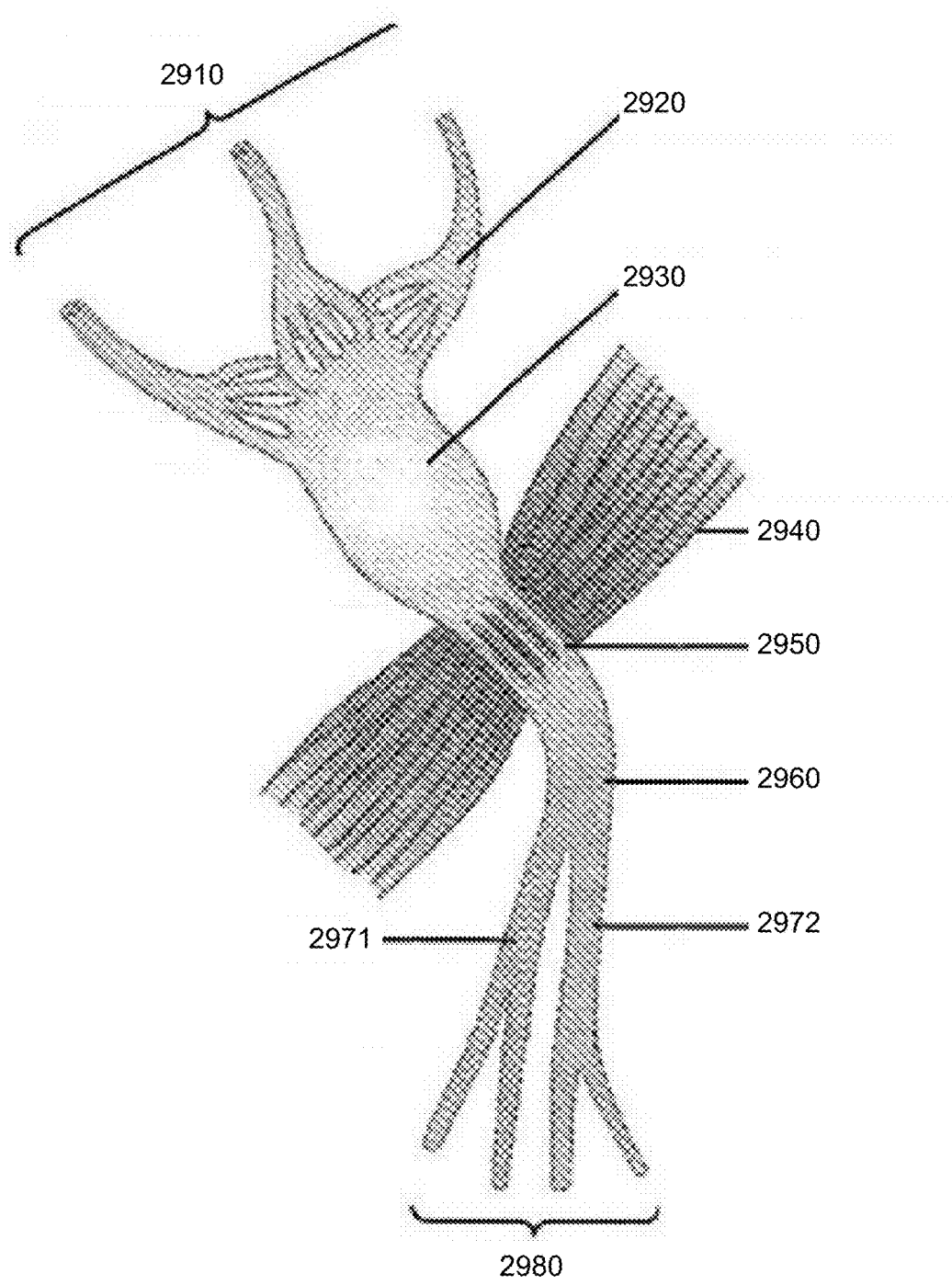
FIG. 29 is an exemplary diagram of the anatomy of the self-conducting system of a heart, in accordance with various embodiments.

FIG. 29 is an exemplary diagram 2900 of the anatomy of the self-conducting system of a heart, in accordance with various embodiments. The self-conducting system begins with S-A node (SAN) 2910. Conduction moves from SAN 2910 through transitional fibers 2920 to A-V node (AVN) 2930. Conduction then moves from AVN 2930 past atrioventricular fibrous tissue 2940 and through penetrating portion of A-V bundle (His bundle) 2950 to distal portion of A-V bundle 2960. From distal portion of A-V bundle 2960 conduction moves through right bundle branch 2971 and left bundle branch 2972 to ventricular septum 2960.

Figure 30:
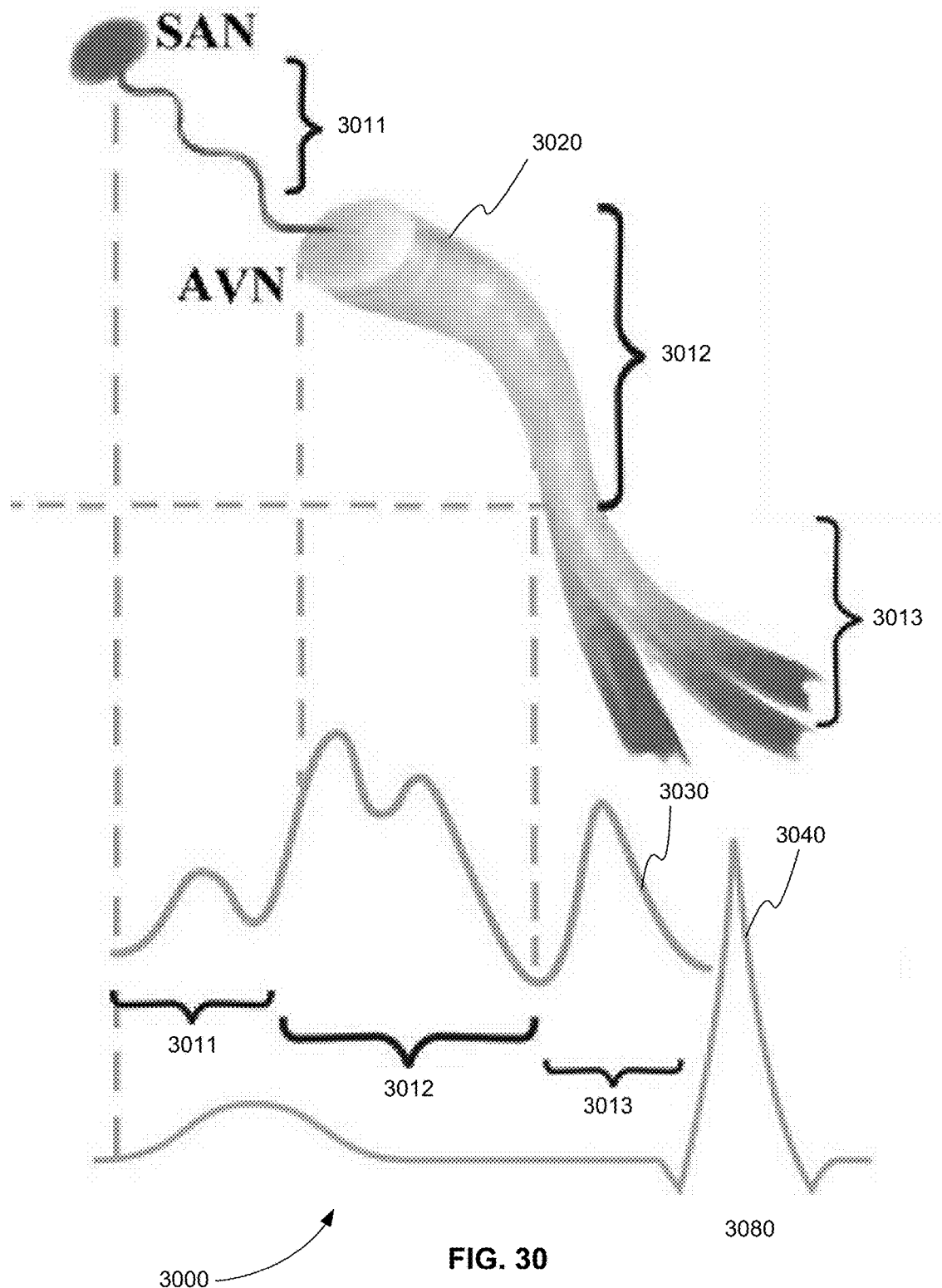
FIG. 30 is an exemplary diagram showing the anatomic sites that the PA, AH, and HV intervals represent and the corresponding PA, AH, and HV intervals in a saah ECG waveform and traditional ECG waveform, in accordance with various embodiments.

FIG. 30 is an exemplary diagram 3000 showing the anatomic sites that the PA, AH, and HV intervals represent and the corresponding PA, AH, and HV intervals in a saah ECG waveform and traditional ECG waveform, in accordance with various embodiments. PA interval 3011, AH interval 3012, and HV interval 3013 are depicted with respect to anatomic sites along self-conducting system 3020 of the heart. The same intervals, PA interval 3011, AH interval 3012, and HV interval 3013, are also shown with respect to saah ECG waveform 3030 and traditional ECG waveform 3040. FIG. 30 shows that processed or calculated information like PA interval 3011, AH interval 3012, HV interval 3013, and saah ECG waveform 3030 relate ECG signals more closely to the anatomy of self-conducting system 3020 than traditional ECG waveform 3040.

Figure 31:
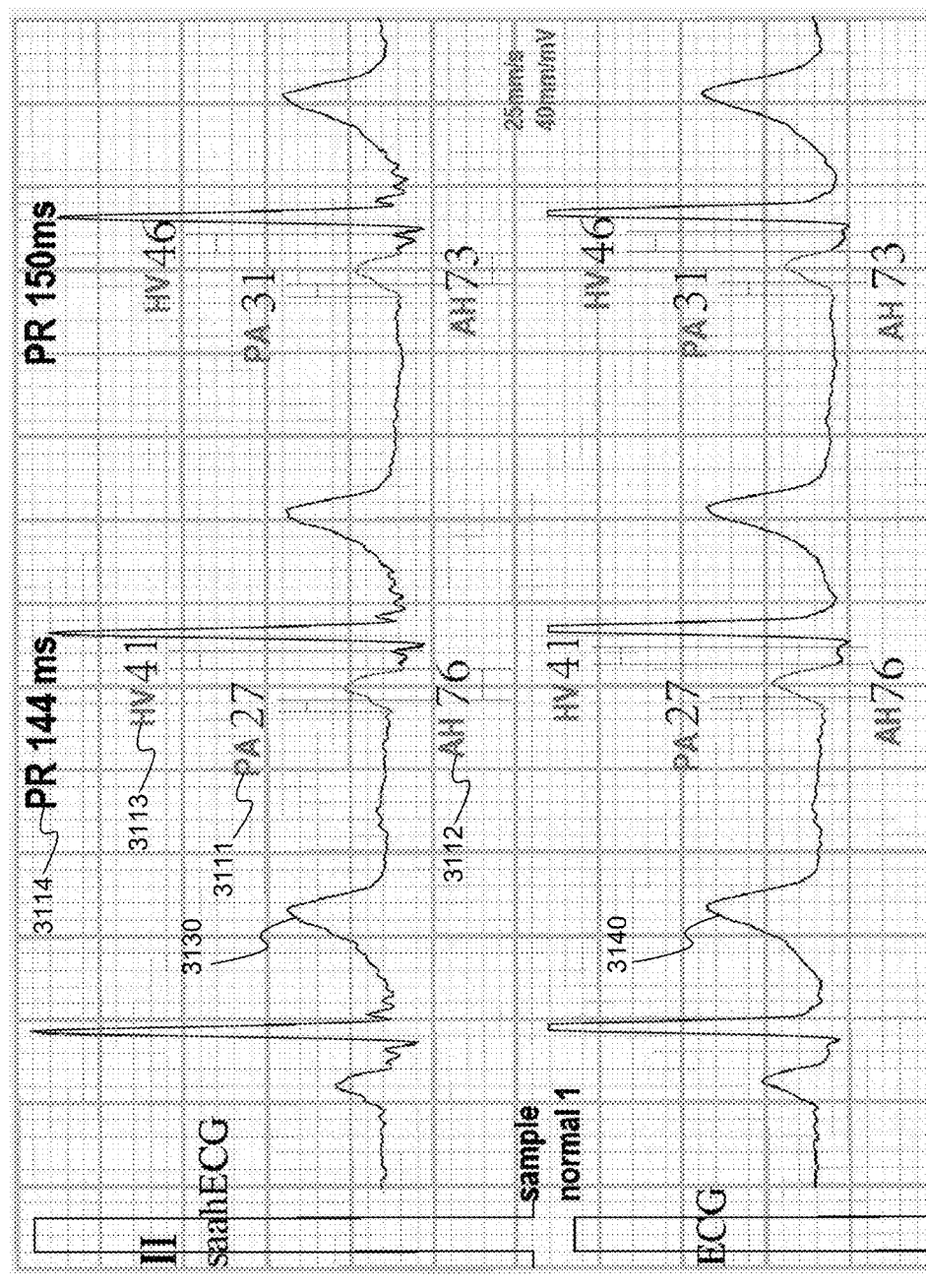
FIG. 31 is an exemplary comparison plot of a saah ECG waveform and a traditional ECG waveform with PA, AH, HV, and PR interval values obtained from aiECG processing for a patient with a normal heart, in accordance with various embodiments.

FIG. 31 is an exemplary comparison plot 3100 of a saah ECG waveform and a traditional ECG waveform with PA, AH, HV, and PR interval values obtained from aiECG processing for a patient with a normal heart, in accordance with various embodiments. Timing values for PA interval 3111, AH interval 3112, HV interval 3113 and PR interval 3114 are shown with respect to saah ECG waveform 3130 and aligned traditional ECG waveform 3140. As described above, PR interval 3114 refers to the time period that includes the P waveform and the PR segment of traditional ECG waveform 3140. FIG. 31 shows that processed or calculated information like the timing values for PA interval 3111, AH interval 3112, HV interval 3113, and PR interval 3113 and saah ECG waveform 3130 provide much more information than traditional ECG waveform 3140 on its own. Plot 3100 is the type of information that server computer server 2220 of FIG. 22 is adapted or configured to allow at least one client device 2230 of FIG. 22 to access.

Figure 32:
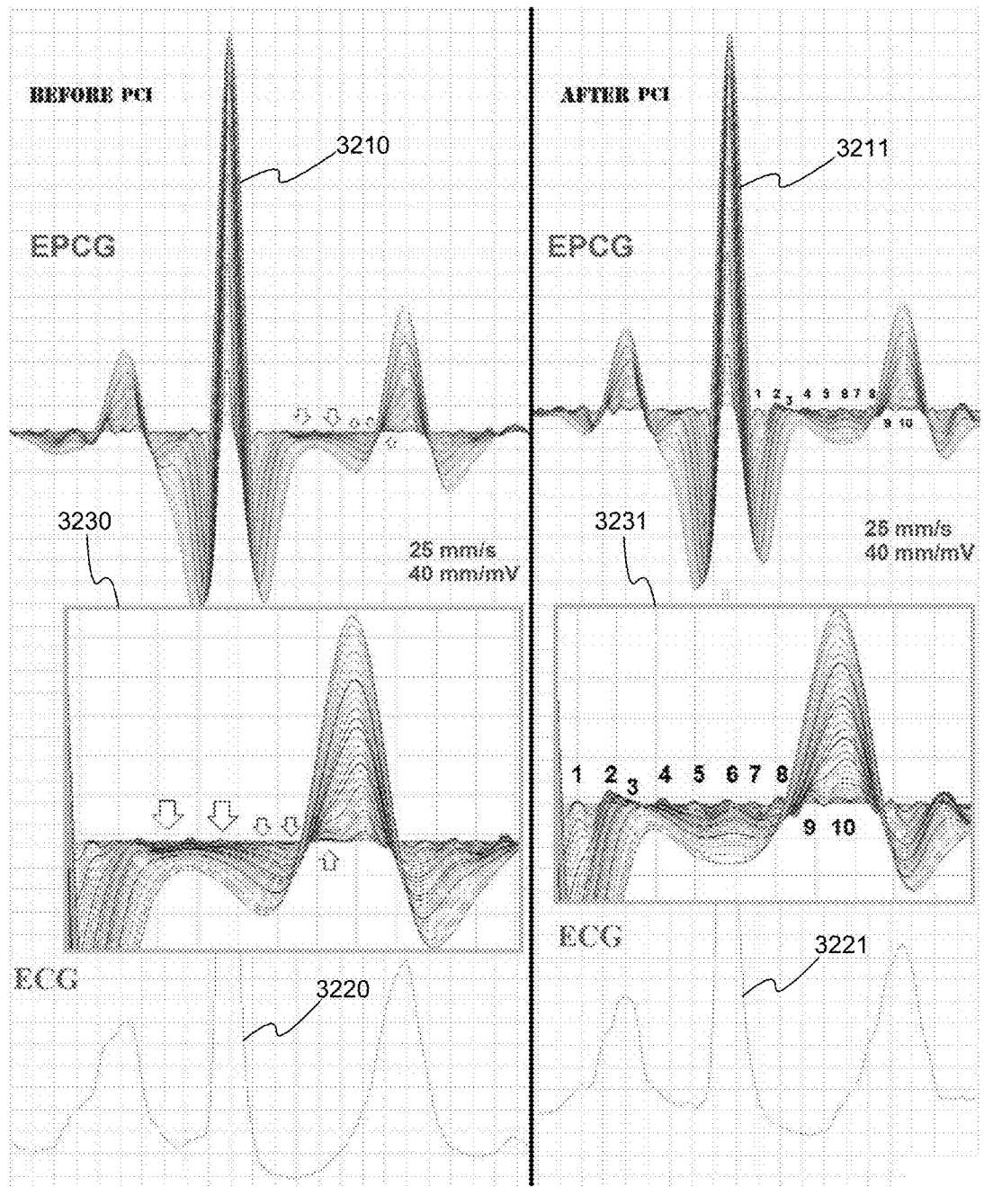
FIG. 32 is an exemplary comparison plot of a multi-domain ECG or electrophysiocardiogram (EPCG) waveform aligned with a traditional ECG waveform for a patient with acute coronary syndrome (ACS) before and after percutaneous coronary intervention (PCI), in accordance with various embodiments.

FIG. 32 is an exemplary comparison plot 3200 of a portion of a multi-domain ECG or electrophysiocardiogram (EPCG) waveform aligned with a portion of a traditional ECG waveforms for a patient with acute coronary syndrome (ACS) before and after percutaneous coronary intervention (PCI), in accordance with various embodiments. EPCG waveform 3210 is aligned with traditional ECG waveform 3220 for the patient with ACS before PCI treatment. EPCG waveform 3211 is aligned with traditional ECG waveform 3221 for the patient with ACS after PCI treatment. A comparison of magnified portions 3230 and 3231 of EPCG waveforms 3211 and 3211, respectively, shows that all small waveforms are not apparent in waveform portion 3210 before PCI treatment are back to normal after PCI treatment in waveform portion 3211. Similar information cannot be found in a comparison of traditional ECG waveforms 3220 and 3221. Plot 3200 is also the type of information that server computer server 2220 of FIG. 22 is adapted or configured to allow at least one client device 2230 of FIG. 22 to access.

Figure 33:
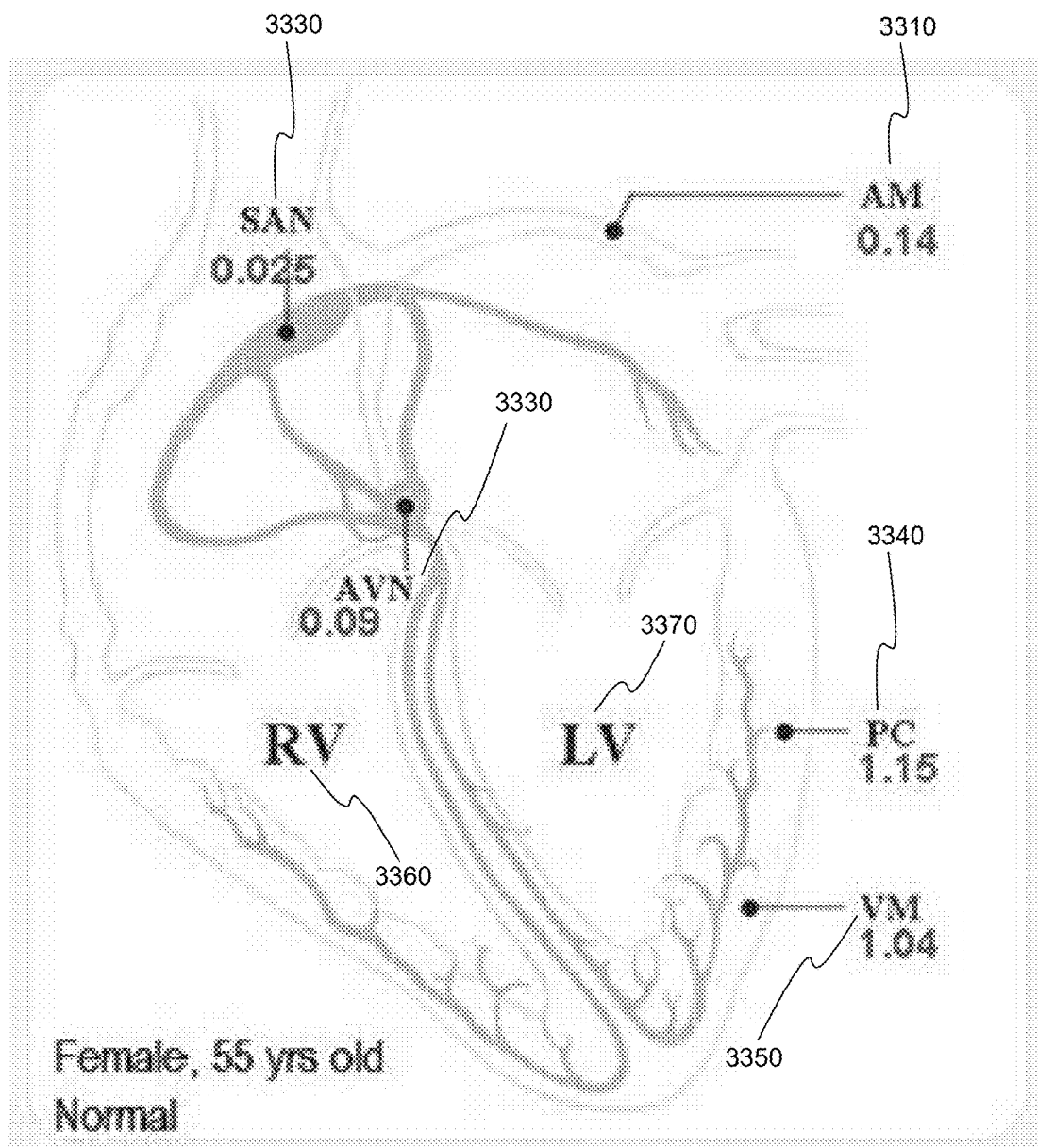
FIG. 33 is an exemplary diagram showing timing values of conduction calculated at various anatomic sites along the self-conduction system of a normal heart by further processing a traditional ECG waveform, in accordance with various embodiments.

FIG. 33 is an exemplary diagram 3300 showing timing values of conduction calculated at various anatomic sites along the self-conduction system of a normal heart by further processing a traditional ECG waveform, in accordance with various embodiments. For example, timing values are provided for the atrial myocardium (AM) 3310, the sino atrial node (SAN) 3320, the atrioventricular node (AVN) 3330, Purkinje's cell (PC) 3340, and the ventricular myocardium (VM) 3350. The right ventricle (RV) 3360 and the left ventricle (LV) 3370 are also labeled in diagram 3300. Diagram 3300 also depicts the type of information that server computer server 2220 of FIG. 22 is adapted or configured to allow at least one client device 2230 of FIG. 22 to access.

System for Detecting and Processing PCG and ECG Waveforms

Returning to FIG. 22, system 2200 is a noninvasive system for detecting and processing phonocardiogram (PCG) and electrocardiography (ECG) waveforms, in accordance with various embodiments. Electronic acoustic stethoscope 2210 includes earpiece 2211 and chestpiece 2212. Chestpiece 2212, in turn, includes an acoustic transducer (not shown), at least four electrodes (not shown), a wireless communication device (not shown), and at least one processor (not shown).

The at least one processor can be, but is not limited to, a custom integrated circuit, a general purpose microprocessor or micro-controller, or a computer such as the process of FIG. 1.

The acoustic transducer is adapted to contact the skin of a patient, measure heart sounds of the patient, and send the heart sounds to earpiece 2211. The heart sounds are sent electronically to earpiece 2211 using one or more speakers or are sent acoustically through the tubing of electronic acoustic stethoscope 2210, for example. The at least one processor is adapted to create a PCG waveform of the heart sounds.

The at least four electrodes are adapted to contact the skin of the patient and measure heart electrical signals of the patient. The at least one processor is adapted to create an ECG waveform of the heart electrical signals. The wireless communication device is adapted to transmit the PCG waveform and/or the ECG waveform Server computer 2220 is adapted to receive the PCG waveform and/or the ECG waveform from the wireless communication device, process the PCG waveform for additional PCG information, process the ECG waveform for additional ECG information, and provide access to the additional PCG information and/or additional ECG information to at least one client device 2230.

Server computer 2220 can include one or more computer systems that store, process, and serve data. Server computer 2220 can be referred to as the cloud, in a cloud computing scenario.

In various embodiments, the acoustic transducer includes a diaphragm adapted to contact the skin. Further, acoustic transducer can include a microphone or piezoelectric device.

In various embodiments, the at least four electrodes can include metal contacts made of gold or silver that are placed noninvasively on top of a patient's skin. In various alternative embodiments, the at least four electrodes include disposable pad like tabs. Disposable pads can be used because certain jurisdictions or countries do not allow the reuse of electrodes from patient to patient.

In various embodiments, the at least four electrodes are located on extendable arms to allow the electrodes to contact the skin of patients with larger surface areas at more distant locations. The extendable arms can include extendable coils, for example.

In various embodiments, chestpiece 2212 includes display 2213. Display 2213 is used, for example, to display the PCG waveform and/or the ECG waveform. Chestpiece 2212 can also include a switch or touch screen to signal the wireless communication device to transmit the PCG waveform and/or the ECG waveform.

In various embodiments, the additional ECG information provided by server computer 2220 includes a saah ECG waveform. The saah ECG waveform can include information corresponding to the six leads, aVR, aVF, aVL, I, II, and III, of a traditional ECG waveform.

In various embodiments, the additional ECG information provided by server computer 2220 can include a multi-domain ECG waveform and/or aiECG information. The aiECG information can include quantitative information for the P-A (pacing to atrial) interval, A-H (atrial to atrioventricular node) interval, and H-V (His bundle to ventricles) interval, for example.

In various embodiments, the wireless communication device is adapted to transmit the PCG waveform and/or the ECG waveform using the WiFi wireless protocol or the 4G or 5G wireless cellular protocol.

In various embodiments, at least one client device 2230 can include a cellphone, tablet computer, or laptop computer.

In various embodiments, server computer 2220 is adapted to provide access to the additional PCG information and/or additional ECG information to at least one client device 2230 by providing access to a software application (app) on at least one client device 2230. The app is an Android app or iOS app, for example.

Method for Detecting and Processing PCG and ECG Waveforms

Figure 34:
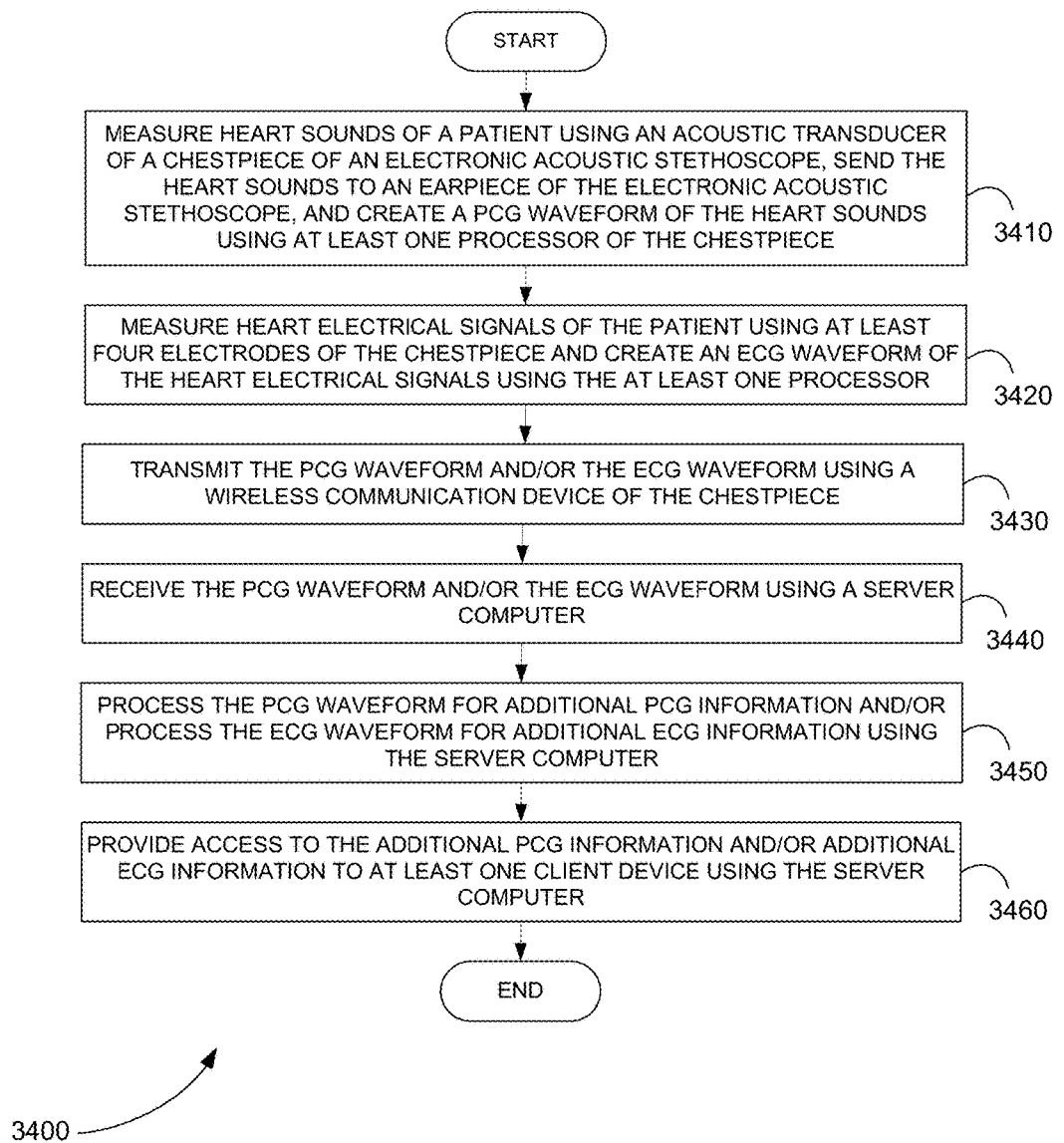
FIG. 34 is a flowchart showing a method for detecting and processing PCG and ECG waveforms, in accordance with various embodiments.

FIG. 34 is a flowchart showing a method 3400 for detecting and processing PCG and ECG waveforms, in accordance with various embodiments.

In step 3410 of method 3400, heart sounds of a patient are measured using an acoustic transducer of a chestpiece of an electronic acoustic stethoscope, the heart sounds are sent to an earpiece of the electronic acoustic stethoscope, and a PCG waveform of the heart sounds is created using at least one processor of the chestpiece.

In step 3420, heart electrical signals of the patient are measured using at least four electrodes of the chestpiece and an ECG waveform of the heart electrical signals is created using the at least one processor.

In step 3430, the PCG waveform and/or the ECG waveform are transmitted using a wireless communication device of the chestpiece.

In step 3440, the PCG waveform and/or the ECG waveform are received using a server computer.

In step 3450, the PCG waveform is processed for additional PCG information and/or the ECG waveform is processed for additional ECG information using the server computer.

Finally, in step 3460, access to the additional PCG information and/or additional ECG information is provided to at least one client device using the server computer.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A noninvasive system for detecting and processing phonocardiogram (PCG) and electrocardiography (ECG) waveforms, comprising:

an electronic acoustic stethoscope that includes an earpiece and a chestpiece, wherein the chestpiece includes an acoustic transducer, at least four electrodes, a wireless communication device, and at least one processor, wherein the acoustic transducer is adapted to contact skin of a patient, measure heart sounds of the patient, and send the heart sounds to the earpiece and the at least one processor is adapted to create a PCG waveform of the heart sounds, wherein the at least four electrodes are adapted to contact the skin of the patient and measure heart electrical signals of the patient and the at least one processor is adapted to create an ECG waveform of the heart electrical signals, wherein the wireless communication device is adapted to transmit the PCG waveform and the ECG waveform; and a server computer that is adapted to receive the PCG waveform and the ECG waveform from the wireless communication device, process the PCG waveform for additional PCG information, process the ECG waveform for additional ECG information, and provide access to the additional PCG information and additional ECG information to at least one device adapted to be a client device, wherein the server computer further includes a signal processor that receives the ECG waveform, individually detects five ECG subwaveforms within the PR interval of the ECG waveform that represent depolarization of a sinoatrial node (SAN), an atria (right atrium (RA) and left atrium (LA)), an atrioventricular node (AVN), a bundle of His (HIS), and bundle branches (BB), respectively, using five predetermined frequency ranges experimentally found for the SAN, the RA and LA, the AVN, the HIS, and the BB, combines the five ECG subwaveforms, and replaces the PR interval of the ECG waveform with the combined five ECG subwaveforms, producing a processed ECG waveform that includes the combined five individual ECG subwaveforms in place of the PR interval.

2. The ECG system of claim 1, wherein the acoustic transducer includes a diaphragm adapted to contact the skin.

3. The ECG system of claim 1, wherein the acoustic transducer includes a microphone.

4. The ECG system of claim 1, wherein the acoustic transducer includes a piezoelectric device.

5. The ECG system of claim 1, wherein the at least four electrodes include metal contacts made of gold or silver.

6. The ECG system of claim 1, wherein the at least four electrodes include disposable pad like tabs.

7. The ECG system of claim 1, further comprising four extendable arms that include the at least four electrodes.

8. The ECG system of claim 7, wherein the four extendable arms include extendable coils.

9. The ECG system of claim 1, wherein the chestpiece includes a switch or touch screen to signal the wireless communication device to transmit the PCG waveform and the ECG waveform.

10. The ECG system of claim 1, wherein the processed ECG waveform includes information corresponding to the six leads, aVR, aVF, aVL, I, II, and III, of a traditional ECG waveform.

11. The ECG system of claim 1, wherein the additional ECG information includes a multi-domain ECG waveform.

12. The ECG system of claim 1, wherein the additional ECG information includes quantitative information for the P-A (pacing to atrial) interval, A-H (atrial to atrioventricular node) interval, and H-V (His bundle to ventricles) interval.

13. The ECG system of claim 1, wherein the wireless communication device is adapted to transmit the PCG waveform and the ECG waveform using the WiFi wireless protocol or the 4G or 5G wireless cellular protocol.

14. The ECG system of claim 1, wherein the server computer that is adapted to provide access to the additional PCG information and additional ECG information to the at least one device by providing access to a software application on the at least one device.

15. The ECG system of claim 14, wherein the software application is an Android application or iOS application.

16. A noninvasive method for detecting and processing phonocardiogram (PCG) and electrocardiography (ECG) waveforms:
measuring heart sounds of a patient using an acoustic transducer of a chestpiece of an electronic acoustic stethoscope, sending the heart sounds to an earpiece of the electronic acoustic stethoscope, and creating a PCG waveform of the heart sounds using at least one processor of the chestpiece;
measuring heart electrical signals of the patient using at least four electrodes of the chestpiece and creating an ECG waveform of the heart electrical signals using the at least one processor;
transmitting the PCG waveform and the ECG waveform using a wireless communication device of the chestpiece;
receiving the PCG waveform and the ECG waveform using a server computer;
processing the PCG waveform for additional PCG information and processing the ECG waveform for additional ECG information using the server computer;
providing access to the additional PCG information and additional ECG information to at least one device adapted to be a client device using the server computer; and
individually detecting five ECG subwaveforms within the PR interval of the ECG waveform that represent depolarization of a sinoatrial node (SAN), an atria (right atrium (RA) and left atrium (LA)), an atrioventricular node (AVN), a bundle of His (HIS), and bundle branches (BB), respectively, using five predetermined frequency ranges experimentally found for the SAN, the RA and LA, the AVN, the HIS, and the BB, combining the five ECG subwaveforms, and replacing the PR interval of the ECG waveform with the combined five ECG subwaveforms using a signal processor of the server computer, producing a processed ECG waveform that includes the combined five individual ECG subwaveforms in place of the PR interval.

\* \* \* \* \*